United States Patent [19]
Chait et al.

[11] Patent Number: 6,136,960
[45] Date of Patent: Oct. 24, 2000

[54] METHOD FOR EVALUATION OF THE RATIO OF AMOUNTS OF BIOMOLECULES OR THEIR SUB-POPULATIONS IN A MIXTURE

[75] Inventors: Arnon Chait, 408 Glen Park Dr., Bay Village, Ohio 44140; Boris Y. Zaslavsky, 34200 Country View La., Solon, Ohio 44139

[73] Assignees: Boris Y. Zaslavsky, Solon; Arnon Chait, Bay Village, both of Ohio

[21] Appl. No.: 09/135,751

[22] Filed: Aug. 18, 1998

Related U.S. Application Data

[63] Continuation-in-part of application No. 09/050,480, Mar. 30, 1998, abandoned, which is a continuation of application No. 08/635,384, Apr. 19, 1996, Pat. No. 5,734,024.
[60] Provisional application No. 60/056,158, Aug. 19, 1997.
[51] Int. Cl.$^7$ .......................... G01N 33/53; G01N 21/00; G01N 31/00; C07C 1/02; G07D 231/00
[52] U.S. Cl. ............................ 530/412; 435/2; 435/7.1; 435/7.4; 435/262; 435/41; 435/810; 435/813; 435/289.1; 435/283.1; 435/304; 436/66; 436/63; 436/8; 436/15; 436/174; 436/177; 436/536; 436/538; 422/61; 210/634; 210/635; 210/639; 548/104; 548/108; 548/403
[58] Field of Search .................................. 433/2, 7.1, 7.4, 433/41, 262, 810, 813, 289.1, 283.1, 304; 436/66, 8, 63, 15, 174, 177, 536, 538; 422/61; 210/634, 635, 639; 548/104, 108, 403; 530/412, 417, 422

[56] References Cited

U.S. PATENT DOCUMENTS

| | | | |
|---|---|---|---|
| 4,269,605 | 5/1981 | Dean et al. | 23/230 |
| 4,690,892 | 9/1987 | Ananthapadmanabhan et al. | 435/183 |
| 5,283,339 | 2/1994 | Arnold et al. | 548/104 |
| 5,407,810 | 4/1995 | Builder et al. | |
| 5,510,247 | 4/1996 | Komives et al. | 435/41 |
| 5,514,592 | 5/1996 | Schoener et al. | 436/66 |

OTHER PUBLICATIONS

Morris, et al. Separation Methods in Biochemistry, published 1976, Pitnam Publishing, London, pp. 361–412 and 990–992.

Database Dialog, Derwent Biotechnology Abstracts Accession No. 93–07279. Chai, et al. Partition of proteins in aqueous two-phase systems containing charged dextran or hydrophobic PEG–protein purification by phase partitioning in an aqueous two-phase system. Biotechnology Techniques. 1993, vol. 7, No. 5, pp. 373–378.

Database Medline Dialog, Abstract Accession No. 96330460, Sorvajarvi et al. Sensitivity and specificity of carbohydrate-deficient transferrin as a marker of alcohol abuse are significantly influenced by alterations in serum transferrin: comparison of two methods. Alcohol Clinical Experimental Research. May 1996, vol. 20, No. 3, pp. 449–454.

(List continued on next page.)

*Primary Examiner*—James C. Housel
*Assistant Examiner*—Gailene R. Gabel
*Attorney, Agent, or Firm*—Fay, Sharpe, Fagan, Minnich & McKee, LLP

[57] ABSTRACT

The present invention is directed to a method of determining the ratio of the concentration or amounts of two or more chemical compounds and/or biopolymers, or of the relative amounts of sub-populations of closely structurally related compounds, in a multi-component mixture, extract, system, and the like using an analytical physicochemical process. The method is based on distribution of the components of the mixture (system, extract, etc.) between two or more immiscible phases and the subsequent determination of the total amounts (concentrations) of biopolymers (chemical compounds) or of the amounts (concentrations) of one or more component(s) or sub-populations of the system in the phases. The ratio between these concentrations is defined therein as the partition coefficient. The partition coefficient is used as a measure of the ratio of the amounts of two or more biopolymers (chemical compounds) or their sub-populations in a multi-component mixture (extract, system, etc.), when calibrated against a series of sample systems of the same type with varied ratios of components.

15 Claims, 10 Drawing Sheets

OTHER PUBLICATIONS

Database FEDRIP Dialog, Federal Research in Progress, Dialog Accession No. 00267315, Analiza, Inc., "New Method for Measurement of CDT Level in Serum, " Identifying No. 39527, Agency Code SBIR.

Zaslovsky et al. Biochim. Biophys. Acta 579:463–465, 1979.

Wingun et al. J. Chromatog. B. 680:113–122, 1996.

Johansson, G. in Walter et al. (Ed) Partitioning in Aqueous Two–Phase Systems Acad. Press, Orlando, FL 161–226, 1985.

Zaslovsky, et al. B.Y. Aqueous Two–Phase Partitioning Marcel Dekker, Inc., New York. pp. 401–446, 1995.

Mattiasson et al. Partition Affinity Ligand Assay (PALA) for Quantitation of Triiodothyronine in Serum. Clinical Chemistry. April 1982, vol. 28, No. 4, pp. 608–683.

Sodergard et al. Calculation of Free and Bound Fractions of Testosterone and Estradiol–17βto Human Plasma Proteins at Body Temperature. Journal of Steroid Biochemistry. 1982, vol. 16, pp. 801–810.

Bearden. Quantitation of Submicrogram Quantities of Protein by an Improved Protein–Dye Binding Assay. Biochimica et Biophysical Acta. 1978, vol. 533, pp. 535–529.

Walter et al. Partition of Closely Related Proteins in Aqueous Two–Polymer Phase Systems. Human Hemoglobin Variants and Hemoglobins from Different Species, Biochemistry. 1971, vol. 10, No. 1, pp. 108–112.

Zaslavsky, et al. Possibility of Analytical Application of the Partition in Aqueous Biphasic Polymeric Systems Technique. Biochimica et Biophysical Acta. 1978, vol. 510, pp. 160–197.

Walter, et al. Partitioning in Aqueous Two–Phase Systems: Theory, Methods, Uses and Applications to Biotechnology, published 1985 by Academic Press, Inc., Orlando, pp. 161–226 and 529–587.

METHOD FOR EVALUATION OF THE RATIO OF AMOUNTS OF BIOMOLECULES OR THEIR SUB-POPULATIONS IN A MIXTURE

CROSS REFERENCES TO RELATED APPLICATIONS

This application claims priority to the filing date of provisional application Ser. No. 60/056,158, filed Aug. 19, 1997, and also is a continuation-in-part of U.S. application Ser. No. 09/050,480, filed Mar. 30, 1998 (now abandoned), which is a continuation of U.S. application Ser. No. 08/635,384, filed Apr. 19, 1996 (now U.S. Pat. No. 5,734,024).

FIELD OF INVENTION

This invention is directed to a method for assessing the ratios of amounts of biological molecules or their sub-populations in a mixture, extract, and/or system. Sub-populations are defined herein as groups of biological molecules that are structurally-related in regard to a certain characteristic, such as electrophoretic mobility, pI value, relative content of a particular chemical moiety or type of moieties. This method can be utilized for analysis and/or characterization of chemical compounds, biological materials, extracts, and mixtures; quality control and in-process monitoring of biological products, biopharmaceuticals, and multi-component biological systems; medical diagnosis, pathology, toxicology, drug safety studies and related purposes. However, it will be appreciated that the invention has broader applications and may be advantageously employed in other environments and applications.

BACKGROUND OF THE INVENTION

Information concerning the ratio(s) of concentration or amount of chemical compounds, including biological molecules such as proteins, glycoproteins, nucleotides, and the like, in a multi-component mixture, extract, system, etc., or the ratio of the amount of sub-populations of such biological molecules, is important in order to identify and characterize the mixture, extract, and/or system. This information is useful for the characterization of raw materials and/or end products in manufacturing of biologicals and biopharmaceutical agents; in-process monitoring of biotechnology products; quality control of multi-component biopharmaceuticals, such as vaccines, for diagnosis, prognosis, and monitoring of diseases and response to treatment, for non-morphological evaluation of tissues and body fluids in pathological analysis, etc. This information is also important in toxicology, forensic medicine, drug safety studies, and other fields of biomedicine.

Hereafter, the word biopolymer should be taken as a descriptive word for compounds of biological origin, such as proteins, enzymes, nucleic acids, polynucleotides, peptides and the like, and derivatives of such compounds. Analysis of a mixture of chemical compounds and/or biopolymers is generally based on separation of the mixture into its individual components. The separation process immediately precedes or is concurrent with the measurement of the level of the individual components. Separation procedures currently used in analytical determinations include liquid chromatography, electrophoresis, electrofocusing, and the like. These procedures are generally time- and labor-consuming, expensive, and are customarily performed by highly-skilled personnel.

Sometimes only the ratio of the amounts of two biopolymers or sub-populations of different molecular forms of the same biopolymer in a multi-component system is of interest. Several distinct forms of a protein are often present in a biological fluid such as blood, urine, etc. These forms may differ by a number of certain residues, such as sialic acids or glucose residues, by glycosylation pattern, by occurrence as free individual molecules vs. complexes with certain ligands. A biopolymer simultaneously existing in different molecular forms may be viewed, for the purpose of this invention, as a population consisting of two or more sets of sub-populations. The ratio of the amounts of these sub-populations is often important for medical diagnostics, quality control, and other applications.

In certain applications, including medical diagnostics, it is often useful to compare a population of biomolecules to a reference population, or to compare a sub-population to a reference sub-population. Hereinafter both cases are referred to as sub-population. In this context, the ratio of the amounts of sub-populations refers to a quantitative measure of the difference between a sample comprising of a sub-population (s) and a reference sample. For these applications it is also possible to use a particular numerical value of the ratio as defined above, as a numerical cut-off value to delineate when a sample comprising of a sub-population(s) of biomolecules could be considered clinically different from a reference sample. Monitoring a change in the ratios of components and/or sub-populations may be of diagnostic value even when information regarding the exact nature of changes in the components and/or subpopulation is not available.

An illustrative example of how the determination of the ratio of the amounts of sub-populations is useful is offered by carbohydrate-deficient transferrin (CDT) detection.

Found in blood serum, modified forms (isoforms) of transferrin (Tf) are proposed as a marker of long-term alcohol abuse. Changes in the structure of the carbohydrate part of the protein Tf, such that the sialic acid content is decreased, are presumed to be indicative of long-term alcohol abuse. Tf is found in the blood as a population comprised of several forms which are different in regard to their sialic acid content and pI value. CDT is also found in the blood to exist as a sub-population of several modified isoforms of Tf, including isoforms with low sialic acid content. The relative amount of these isoforms is increased under alcohol abuse. The ratio of CDT to total Tf that may be indicative of alcohol abuse refers to the relative amount of the sub-population of modified Tf with low sialic acid content to the total amount of all isoforms of Tf.

A second example of how the determination of the ratio of the amounts of sub-populations is useful is by detection and determination of prostate-specific antigen (PSA). Recently, the diagnostic power of the prostate-specific antigen (PSA) analysis has been found to significantly increase when one examines the ratio of the free PSA content in serum to that of the PSA complex with anti-$\alpha_1$-chymotrypsin.

A third example is provided by analysis of the ratio of glycated hemoglobin to total hemoglobin content as an important indicator of the long-term status of diabetes. Since glycated hemoglobin may refer to a sub-population comprising different molecular forms of hemoglobin, it is the ratio of the amount of that sub-population to the total amount of hemoglobin (total population of all isoforms) in the mixture that is of clinical importance.

In the three examples discussed above it is possible to use the ratio obtained in the present invention to detect a departure of the sub-population from a reference value that is of specific clinical diagnostic value. The utility of the ratio obtained using the present invention would then be to determine, typically using a cut-off value, whether a sample is clinically different from the reference. The level of difference could be delineated from the quantitative value of the ratio between the two samples.

Measurements of all these ratios are generally based on separation of the diagnostically-relevant protein isoforms. An analytical method capable of detecting the ratios in question without first separating the isoforms should be more efficient than known separation-based procedures.

SUMMARY OF THE INVENTION

The present invention provides a new method for quantitative analysis of the ratio of different molecular forms of a protein composition or that of different biopolymers in a multi-component mixture, extract, and/or system. This analysis may be used for characterization of raw materials and/or end products in manufacturing of biologicals and biopharmaceutical agents; for in-process monitoring of biotechnology products, for quality control of multi-component biopharmaceuticals (such as vaccines), for diagnosis, prognosis, and monitoring of diseases and response to the treatment; for non-morphological evaluation of tissues and body fluids in toxicology, pathological and/or forensic analysis, drug safety studies, and the like. These and other objectives of the invention will become apparent in view of the description below.

BRIEF DESCRIPTION OF THE DRAWINGS

The following is a brief description of the drawings which are presented for illustrating the invention and not for the purposes of limiting the same.

DETAILED DESCRIPTION OF THE INVENTION

Figure 1:
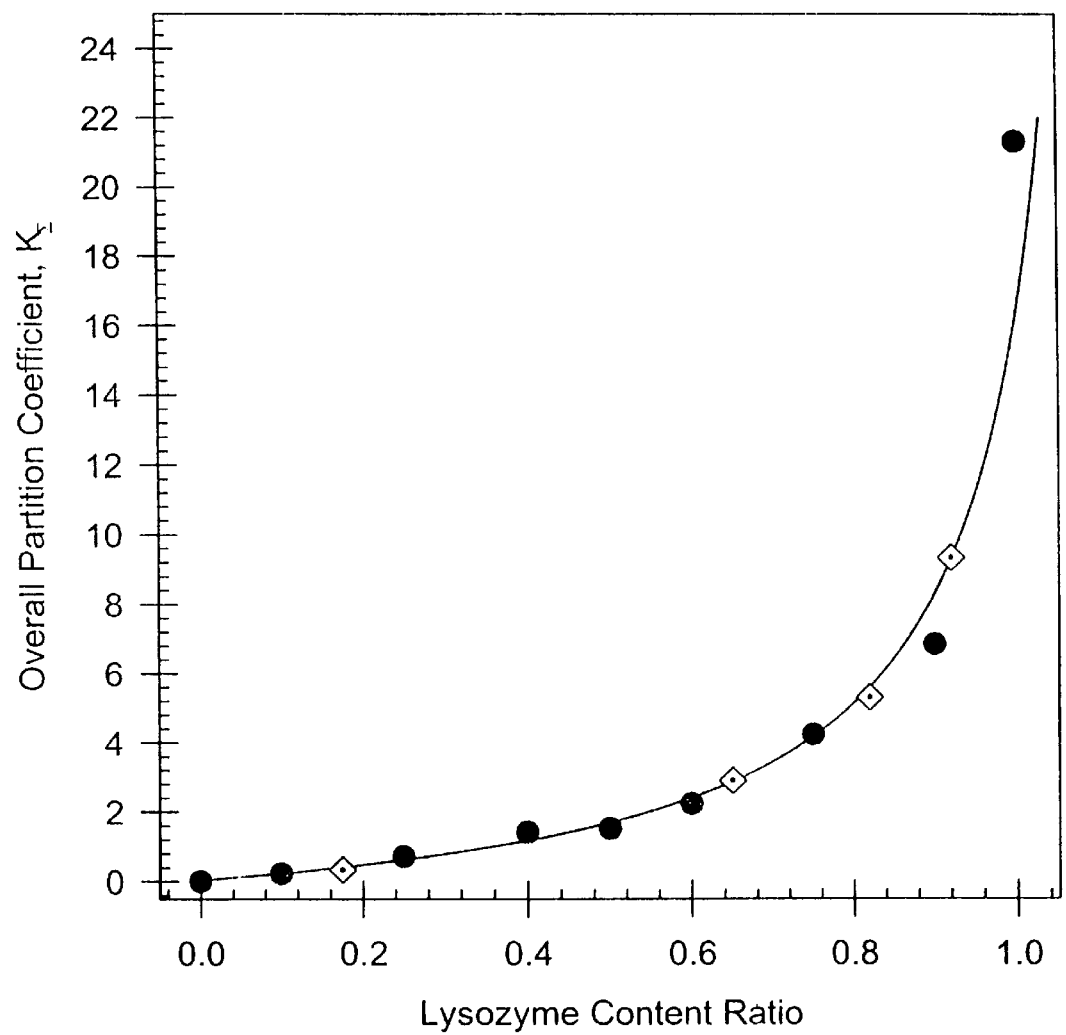
FIG. 1 illustrates the relationship between the overall partition coefficient for the mixture of commercial samples of hen egg white lysozyme and concanavalin A and their ratios in an aqueous two-phase system. The system contained 8.00 wt. % PEG-8000 (with molecular weight of about 8,000), 14.00 wt. % dextran-78 (with molecular weight of about 78,000), and 1.00 M NaCl in 0.015 M sodium/potassium phosphate buffer (pH 5.5). The lysozyme content ratios were 1:0; 9:1; 3:1; 3:2; 1:1; 2:3; 1:3; 1:9; 0:1. The lysozyme content ratio was defined as the ratio of the amount of lysozyme to the total amount of lysozyme and concanavalin A in the mixture (in mg/ml). The protein(s) concentrations in each phase were assayed by measuring the optical absorbance at 280 nm in cuvettes with 10 mm path length. Filled circles represent experimental data obtained with calibration standard mixtures; dotted diamonds represent the experimental data obtained with the separately prepared mixtures of unidentified composition.

Partitioning in an aqueous polymer two-phase system is a highly efficient, versatile, and cost-effective method for characterizing the ratio(s) of the amounts of individual protein isoforms or of two or more proteins, nucleic acids, etc., in a mixture, extract, and/or system. Aqueous two-phase systems arise in aqueous mixtures of different water-soluble polymers or a single polymer and a salt. When two certain polymers, e.g., dextran and polyethylene glycol ("PEG"), are mixed in water above certain concentrations, the mixture separates into two immiscible aqueous phases. A clear interfacial boundary develops; one phase is rich in one polymer and the other phase is rich in the other polymer. The aqueous solvent in both phases provides media suitable for biological products such as proteins. Hereafter the term "aqueous two-phase system" refers to an aqueous system containing two or more distinct phases.

By choosing the type (chemical nature, structure, and molecular weight) and concentration of phase-forming polymers, the properties of the phases can be varied. Additionally, the composition of the phases and their properties may be changed by adding inorganic salts and/or organic additives. Examples of such aqueous two-phase systems useful in the present invention include, but are not limited to, dextran/PEG, dextran/polyvinylpyrrolidone, PEG/salt, and polyvinylpyrrolidone/salt.

When a solute such as a protein is put into such a system, it distributes between the two phases. The procedure is fairly simple and similar to extraction. Solutions of two polymers are mixed and a two-phase system is formed. Centrifugation to speed phase settling may be used to enhance separation of the phases. The partition behavior of a protein may be influenced by many variables, such as pH, polymer and salt composition of the system, temperature, etc.

Partitioning of a solute, such as protein, nucleic acid, etc., is characterized by the partition coefficient, "K", defined as the ratio between the concentrations of the solute in the two immiscible phases. For example, the partition coefficient, K, of a protein is defined as the ratio of the protein in first phase to that in the second phase in a biphasic system. For multi-phase systems there exist more than a single value of the partition coefficient. It is to be understood that the reference to a partition coefficient value for a two-phase system could easily be extended to the analysis of several partition coefficient values. Thus, the entire reference to a partition coefficient value refers, without a loss of generality, to a number of partition coefficients that could be constructed from a multi-phase system.

It is widely recognized that the partition coefficient K for a given biopolymer in the two-phase system of a fixed composition is a constant specific for the biopolymer and independent of the presence of other biopolymers, if their concentrations are sufficiently low and if they do not interact with each other. This fact is important for the intended analytical applications of the technique since it enables a direct measurement of the intended ratio using a multi-component mixture of different biopolymers, extract, and/or system without prior separation. The partition coefficient of a single biopolymer in a mixture of different biopolymers can be measured using concentration assay highly specific for this particular biopolymer, such as, e.g., immunoassay.

If a mixture of two biopolymers is composed of two different biopolymers and they do not interact with each other, the biopolymers will independently distribute between the two phases. Each of these two biopolymers will contribute (differently or similarly) into the total biopolymer concentration measured in each phase. Thus, the overall partition coefficient of the mixture will be a function of the ratio of the contents of the two biopolymers in the initial mixture.

When the mixture contains two or more sub-populations of closely structurally-related compounds, the interpretation of the partition coefficient value is similar. In this case, the ratio corresponding to the measured K-value describes the relative amounts of the two (or more) ensemble averages of the sub-populations. The ensemble average of a sub-population is the appropriately weighted average (e.g., by their relative amounts) of the K-value of the individual constituents. The evaluation of the relative amounts of the sub-populations may be of significant analytical merit, e.g., when the K-value reflects the relative amount of a sub-population of disease-indicating isoforms of a particular biomolecule to its native form. When the K-value is used to quantify the relative amounts of sub-populations of biomolecules, it is typically given as a range rather than as a single specific value. This range reflects the naturally occurring range of the individual isoforms present in a particular sub-population. To be diagnostically useful, the aqueous two-phase system should be designed in a way to maximize the difference between the ensemble averages of the sub-populations under consideration that are observed in practice, while minimizing the individual range of each sub-population, i.e., maximize the signal to noise ratio for each particular application.

In order to determine the overall partition coefficient K of a mixture of two biopolymers or their sub-populations, several steps are followed. These steps are system preparation, sample introduction into the system, sufficient mixing of the system together with the sample, phase separation and quantification of the amount of sample in the phases. In a typical process, concentrated stock solutions of all the components (polymer 1, e.g., dextran; polymer 2, e.g., PEG, Ficoll, salts, etc.) in water are prepared separately. The stock solutions of phase polymers, salts, and the biopolymer mixture are mixed in the amounts and conditions (i.e., pH from about 1.0 to about 11.0, temperature from about 4° C. to 60° C., salt concentration from 0.001 to 5 mole/kg) appropriate to bring the system to the desired composition. All the solutions are vigorously shaken. Then the system can be allowed to equilibrate, or it can be centrifuged for 2–30 minutes at about 2000 to 4000 g or higher to speed phase settling. Aliquots of the settled phases are typically withdrawn from both the top and bottom phases and analyzed for the biopolymers concentrations.

Additional methods may be devised and/or currently exist in the literature for mixing, separating, and/or measuring the concentrations within each phase. In particular, modern miniaturization technologies may be adopted to perform one or more of these steps using very small quantities of the compounds and/or system fluids. These methods represent different means to accomplish the technical tasks such as mixing, measuring and quantifying.

Different assay methods may be used to determine the concentration of the biopolymers in each phase. For nucleic acids and polynucleotides the common detection technique is direct spectrophotometry at 260 nm. The most common peptide or protein detection techniques include direct spectrophotometry and dye-binding reactions with Coomassie Blue G-250 or fluorescamine, or other dyes and/or reagents. An immunochemical assay may be used as well, e.g., if the mixture of proteins that is to be analyzed is composed of many different proteins (for example, blood serum or plasma), and the ratio of two close isoforms or of sub-populations of one specific protein is desired.

The concentration of the proteins in each phase is then utilized to determine the partition coefficient, K, of the sample. This number is then compared with known partition coefficient (K) values to determine the ratio of the proteins (or their sub-populations) under analysis. If the total amount of sample and the volumes occupied by each phase are known, then it is also possible to determine the K-value by measuring the amount of sample in only one of the phases.

The present invention is further illustrated by the following detailed examples. It is to be understood that the invention is not limited to these examples, and various changes and modifications, e.g., the means of performing the partitioning, may be made in the invention without departing from the spirit and the scope thereof. These examples are shown to illustrate the generality of the present invention. Table 1 set forth below summarizes some of the key parameters varied in each example and is presented to only highlight different aspects of the present invention.

TABLE 1

Key parameters varied in Examples 1–11.

| Example | Individual/Sub-population | Aqueous Two-Phase System | Assay A/B/EIA* | Type P/LMW* |
|---------|---------------------------|--------------------------|----------------|-------------|
| 1       | I                         | PEG/DEX                  | A              | P           |
| 2       | I                         | PEG/DEX                  | B              | P           |
| 3       | I                         | PEG/Salt                 | A              | P           |
| 4       | I                         | PEG/Salt                 | A              | P           |
| 5       | S                         | PVP/DEX                  | A              | P           |
| 6       | S                         | PEG/Salt                 | A              | P           |
| 7       | I                         | PEG/Salt                 | A              | LMW         |
| 8       | I                         | PEG/Salt                 | A              | LMW         |
| 9       | I                         | PEG/Salt                 | A              | LMW         |
| 10**    | I                         | PEG/Salt                 | A              | P           |
| 11      | S                         | PEG/Salt                 | EIA            | P           |

*As defined below:
A     Direct absorbance
B     Bradford
EIA     Enzyme immunoassay
P     Protein
LMW     Low molecular weight compound
**     Example comparing theoretical analysis with experimental data

EXAMPLES

Example 1

Partitioning of mixtures of lysozyme and concanavalin A in an aqueous two-phase system is related to the ratio of concentration of the proteins in the mixture.

Lysozyme from hen egg white and concanavalin A were purchased from Sigma Chemical Company (St. Louis, Mo., USA) and used without further purification. Stock solutions of individual proteins in water were prepared at the protein concentration of 10.4 mg/ml (lysozyme) and 10.6 mg/ml (concanavalin A). Protein stock solutions were mixed with each other to form standard calibration mixtures of the following lysozyme/concanavalin ratios: 1:0; 9:1; 3:1; 3:2; 1:1; 2:3; 1:3; 1:9; 0:1. These standard calibration protein mixtures as well as solutions of individual proteins were subjected to partitioning in the aqueous dextran-poly (ethylene glycol) two-phase system containing 1.00 M NaCl in 0.015 M sodium/potassium phosphate buffer (pH 5.5).

The aqueous two-phase system contained 8.00 wt. % PEG-8000, 14.00 wt. % dextran-78 (with molecular weight of about 78,000), and 1.00 M NaCl in 0.015 M sodium/ potassium phosphate buffer (pH 5.5). Each system was prepared by mixing the appropriate amounts of stock polymer, salt and buffer solutions by weight into a 100 ×75 mm tube up to a total system weight of 2.00 g. The ratio between the volumes of the two phases of each system was (volume of the top phase to volume of the bottom phase) 9:10. A varied amount (50, 100, 150, 200, and 250 $\mu$l) of a given protein solution or that of a mixture of a given ratio and the corresponding amount (200, 150, 100, 50, and 0 $\mu$l) of water were added to a system. The system was vigorously shaken and centrifuged for 20 min. at about 2000 rpm in a centrifuge with a bucket rotor to speed the phase settling. Tubes were taken out of the centrifuge, and aliquots of 150 $\mu$l from the top and the bottom phases were withdrawn in duplicate and each diluted with 1.850 ml water for further analysis.

Several separately prepared test protein mixtures with unidentified compositions were subjected to partitioning using the above procedure. Hereinafter unidentified compositions required performing the partitioning test in reverse, i.e., obtaining the partition coefficient by performing the test and subsequently using the calibration curve to determine the ratio of the proteins (or sub-populations) in question.

The protein(s) concentrations in each phase were assayed by measuring the optical absorbance at 280 nm in cuvettes with 10 mm path length. The measured absorbance of the aliquots from the top phases were plotted as a function of the absorbance of the aliquots from the bottom phases. The partition coefficient for a given protein or protein mixture was determined as a slope of the linear curve representing the plot. The partition experiments were carried out in duplicate or triplicate.

The partition coefficients for the examined standard calibration mixtures of lysozyme and concanavalin A (represented by filled circles) are plotted in FIG. 1 versus the lysozyme content ratio (defined as the ratio of the amount of lysozyme to the total amount of lysozyme and concanavalin A in the mixture). The data given in FIG. 1 indicate clearly that there is a continuous and unique relationship— calibration curve—between the overall partition coefficient for a protein mixture and the lysozyme content ratio. The partition coefficient values for test mixtures with unidentified composition are represented by dotted diamonds. The compositions of the unidentified test mixtures lie, within experimental error, on the previously constructed calibration curve.

Example 2

Partitioning of mixtures of human serum albumin and human $\gamma$-globulin in an aqueous two-phase system is related to the ratio of the amounts of proteins in the mixture.

Human serum albumin and $\gamma$-globulin were purchased from Sigma Chemical Company (St. Louis, Mo., USA) and used without further purification. Stock solutions of individual proteins in water were prepared at the protein concentration each of 2.0 mg/ml. Protein stock solutions were mixed with each other to form calibration standard mixtures of the following albumin/$\gamma$-globulin ratios: 1:0; 3:1; 1:1; 1:3; 1:4; 1:9; 0:1. These protein mixtures were subjected to partitioning in the aqueous dextran-poly(ethylene glycol) two-phase system containing 3.00 M NaCl in 0.05 M sodium phosphate buffer (pH 6.8).

The aqueous two-phase system contained 8.00 wt. % PEG-8000, 14.00 wt. % dextran-78 (with molecular weight of about 78,000), and 3.00 M NaCl in 0.05 M sodium phosphate buffer (pH 6.8). Each system was prepared by mixing the appropriate amounts of stock polymer, salt, and buffer solutions by weight into a 100 ×75 mm tube up to a total system weight of 2.00 g. The ratio between the volumes of the two phases of the system was (volume of the top phase to volume of the bottom phase) 2:3. A varied amount (50, 75, and 100 $\mu$l) of a given protein solution or that of a mixture of a given ratio and the corresponding amount (200, 175, and 150 $\mu$l) of water were added to a system. The system was vigorously shaken and centrifuged for 20 min. at about 2000 rpm in a centrifuge with a bucket rotor to speed the phase settling. Tubes were taken out of the centrifuge, and samples from the top and the bottom phases were withdrawn. The aliquots of 50, 75, and 100 $\mu$l from the samples of both phases were withdrawn in duplicate and each diluted with water up to 200 $\mu$l of total volume of the final sample to be assayed.

The protein(s) concentrations in each phase were assayed using dye-binding reaction with Coomassie Blue G-250. 800 $\mu$l of Bradford reagent (purchased from Sigma) was added to each final sample and the mixtures were vigorously shaken and maintained at room temperature for about 15 to 20 min. After 15 to 20 min., the optical absorbance at 595 nm in cuvettes with 10 mm path length was measured. The measured absorbance of the aliquots from the top phases was plotted as a function of the absorbance of the aliquots from the bottom phases. The partition coefficient for a given protein or protein mixture was determined as a slope of the linear curve representing the plot. The partition experiments were carried out in duplicate or triplicate.

Several separately prepared test protein mixtures with unidentified composition were subjected to partitioning using the above procedure.

Figure 2:
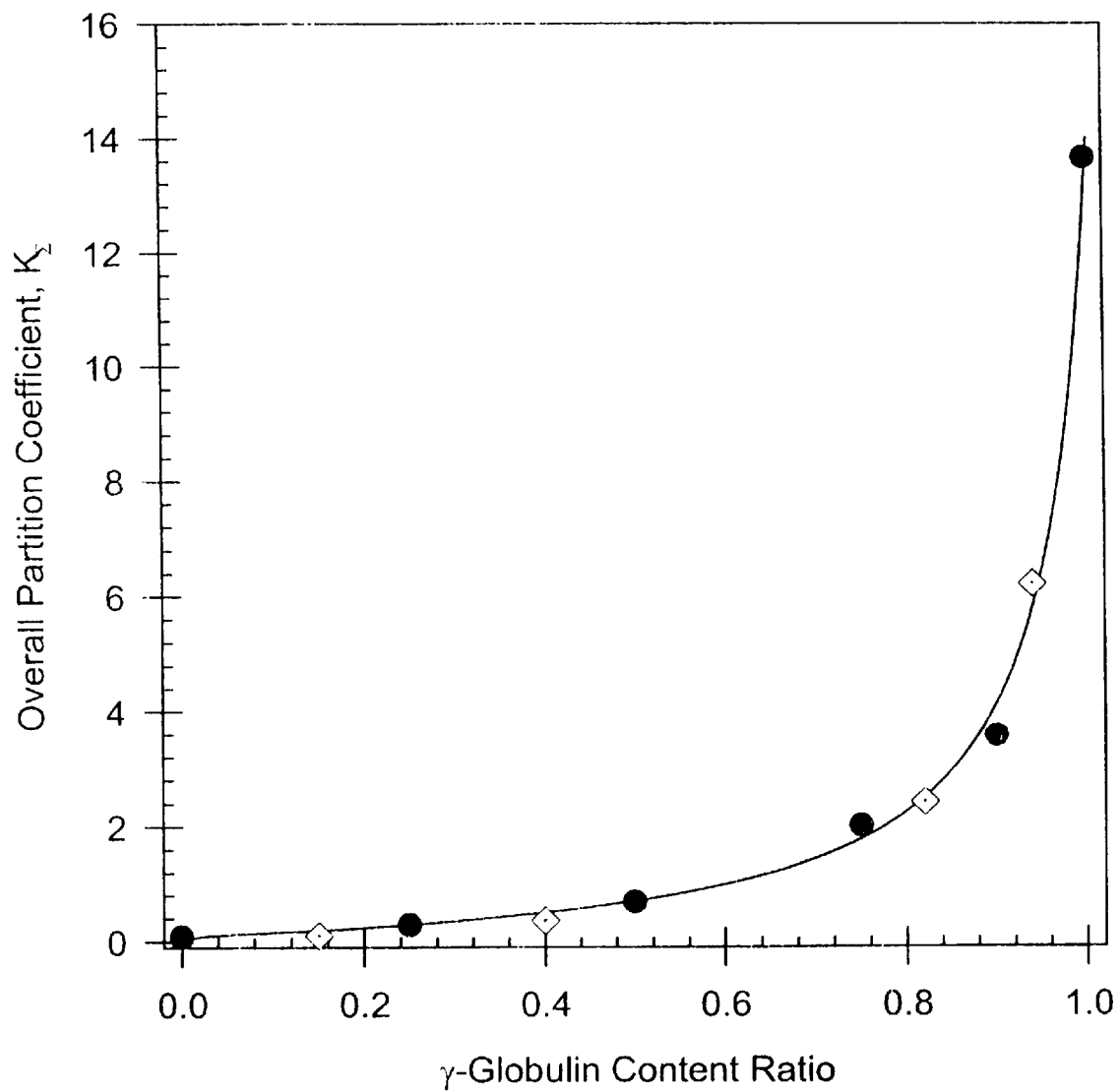
FIG. 2 illustrates the relationship between the overall partition coefficient for the mixture of commercial samples of human serum albumin and γ-globulin and their ratios in an aqueous two-phase system. The system contained 8.00 wt. % PEG-8000 (with molecular weight of about 8,000), 14.00 wt. % dextran-78 (with molecular weight of about 78,000), and 3.00 M NaCl in 0.05 M sodium phosphate buffer (pH 6.8). The γ-globulin content ratios were 1:0; 3:1; 1:1; 1:3; 1:9; 0:1. 1:0; 3:1; 1:1; 1:3; 1:9; 0:1. The γ-globulin content ratio was defined as the ratio of the amount of γ-globulin to the total amount of γ-globulin and albumin in the mixture (in mg/ml). The protein(s) concentrations in each phase were assayed using dye-binding reaction with Coomassie Blue G-250. Filled circles represent experimental data obtained with calibration standard mixtures; dotted diamonds represent the experimental data obtained with the separately prepared mixtures of unidentified composition.

The partition coefficients for the examined standard calibration mixtures of human serum albumin and $\gamma$-globulin (represented by filled circles) are plotted in FIG. 2 versus the $\gamma$-globulin content ratio. The $\gamma$-globulin content ratio is defined as the ratio between the amount of $\gamma$-globulin and the total amount of albumin and $\gamma$-globulin (in mg/ml) in the mixture. The data given in FIG. 2 clearly indicate the existence of a continuous and unique relationship— calibration curve—between the overall partition coefficient for a protein mixture and the ratio of the amounts of protein components in the mixture. The partition coefficient values for test mixtures with unidentified composition are represented by dotted diamonds. The compositions of the unidentified test mixtures lie, within experimental error on the previously constructed calibration curve. It should be indicated that in contrast to measurements in Example 1, the partition coefficients in the present example were obtained using a different protein assay technique. Instead of using a direct measurement of the optical absorbance at 280 nm, the proteins were assayed using the dye-binding reaction with Coomassie Blue G-250. The example provided indicates that the specific technique of the protein concentration assaying is not critical for the subject of the present invention.

Example 3

Partitioning of mixtures of hen egg white lysozyme and human hemoglobin in an aqueous two-phase system is related to the ratio of the amounts of proteins in the mixture.

Lysozyme from hen egg white and human hemoglobin were purchased from Sigma Chemical Company (St. Louis, Mo., USA) and used without further purification. Stock solutions of individual proteins in water were prepared at the protein concentration of 10.0 mg/ml each. Protein stock solutions were mixed with each other to form standard calibration mixtures of the following lysozyme/hemoglobin ratios: 1:0; 3:1; 3:2; 1:1; 2:3; 1:3; 1:9; 0:1. These protein mixtures were subjected to partitioning in the aqueous poly(ethylene glycol)-phosphate buffer two-phase system.

The aqueous two-phase system contained 13.75 wt. % PEG-600 (molecular weight of about 600) and 21.00 wt. % sodium/potassium phosphate buffer (pH 6.5). Each system was prepared by mixing the appropriate amounts of stock polymer and buffer solutions by weight into a 100×75 mm tube up to a total system weight of 2.00 g. The ratio between the volumes of the two phases of each system was as 1:1. A varied amount (200, 250, 300, 350, and 400 $\mu$l) of a given protein solution or that of a mixture of a given ratio and the corresponding amount (200, 150, 100, 50, and 0 $\mu$l) of water were added to a system. The system was vigorously shaken and centrifuged for 30 min. at about 2000 rpm in a centrifuge with a bucket rotor to speed the phase settling. Tubes were taken out of the centrifuge, and aliquots of 150 $\mu$l from the top and the bottom phases were withdrawn in duplicate and each diluted with 1.850 ml water for further analysis.

The protein(s) concentrations in each phase were assayed by measuring the optical absorbance at 280 nm in cuvettes with 10 mm path length. The measured absorbance of the aliquots from the top phases were plotted as a function of the absorbance of the aliquots from the bottom phases. The partition coefficient for a given protein or protein mixture was determined as a slope of the linear curve representing the plot. The partition experiments were carried out in duplicate or triplicate.

Several separately prepared test protein mixtures with unidentified composition were subjected to partitioning using the above procedure.

Figure 3:
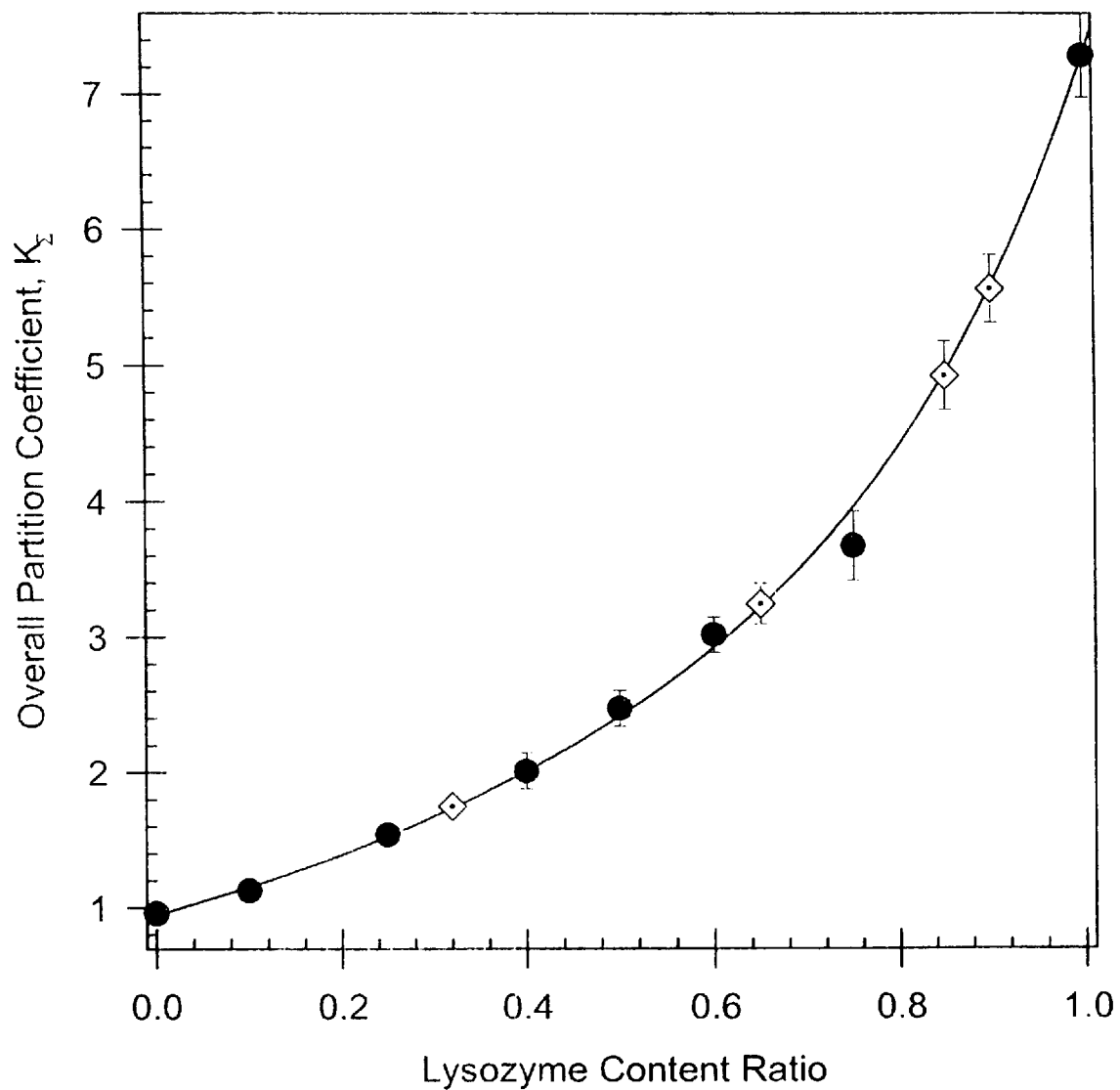
FIG. 3 illustrates the relationship between the overall partition coefficient for the mixture of commercial samples of hen egg white lysozyme and human hemoglobin and their ratios in an aqueous two-phase system. The system contained 13.75 wt. % PEG-600 (with molecular weight about 600), 21.00 wt. % sodium/potassium phosphate buffer (pH 6.5). The lysozyme content ratios were lysozyme/hemoglobin 1:0; 3:1; 3:2; 1:1; 2:3; 1:3; 1:9; 0:1. The lysozyme content ratio was defined as the ratio of the amount of lysozyme to the total amount of lysozyme and hemoglobin in the mixture (in mg/ml). The protein(s) concentrations in each phase were assayed by measuring the optical absorbance at 280 nm in cuvettes with 10 mm path length. Filled circles represent experimental data obtained with calibration standard mixtures; dotted diamonds represent the experimental data obtained with the separately prepared mixtures of unidentified composition.

The partition coefficients for the examined standard calibration mixtures of lysozyme and hemoglobin (represented by filled circles) are plotted in FIG. 3 versus the lysozyme content ratio in the mixtures. The lysozyme content ratio was calculated as the ratio between the amount of lysozyme and the total amount of lysozyme and hemoglobin in each mixture (in mg/ml). The data given in FIG. 3 indicate clearly that there is a continuous and unique relationship—calibration curve—between the overall partition coefficient for a protein mixture and the ratio of the concentration of the two components in the mixture. The partition coefficient values for test mixtures with unidentified composition are represented by dotted diamonds. The compositions of the unidentified test mixtures lie, within experimental error, on the previously constructed calibration curve.

This example illustrates the fact that different aqueous two-phase systems including those formed by a single polymer and inorganic salt(s) may be used for the purpose of the present invention.

Example 4

Partitioning of mixtures of horse myoglobin and bovine $\beta$-lactoglobulin in an aqueous two-phase system is related to the ratio of the amounts of proteins in the mixture.

Horse myoglobin and $\beta$-lactoglobulin from bovine milk were purchased from Sigma Chemical Company (St. Louis, Mo., USA) and used without further purification. Stock solutions of individual proteins in water were prepared at the protein concentration of 10.0 mg/ml each. Protein stock solutions were mixed with each other to form standard calibration mixtures of the following myoglobin/$\beta$-lactoglobulin ratios: 1:0; 9:1; 3:1; 3:2; 1:1; 2:3; 1:3; 1:9; 0:1. These protein mixtures were subjected to partitioning in the aqueous poly(ethylene glycol)-phosphate buffer two-phase system.

The aqueous two-phase system contained 13.75 wt. % PEG-600 (molecular weight of about 600) and 21.00 wt. % sodium/potassium phosphate buffer (pH 6.5). Each system was prepared by mixing the appropriate amounts of stock polymer and buffer solutions by weight into a 100×75 mm tube up to a total system weight of 2.00 g. The ratio between the volumes of the two phases of each system was 1:1. A varied amount (50, 100, 150, 200, and 250 $\mu$l) of a given protein solution or that of a mixture of a given ratio and the corresponding amount (350, 300, 250, 200, and 150 0 $\mu$l) of water were added to a system. The system was vigorously shaken and centrifuged for 30 min. at about 2000 rpm in a centrifuge with a bucket rotor to speed the phase settling. Tubes were taken out of the centrifuge, and aliquots of 200 $\mu$l from the top and the bottom phases were withdrawn in duplicate and each diluted with 2.800 ml water for further analysis.

The protein(s) concentrations in each phase were assayed by measuring the optical absorbance at 280 nm in cuvettes with 10 mm path length. The measured absorbance of the aliquots from the top phases were plotted as a function of the absorbance of the aliquots from the bottom phases. The partition coefficient for a given protein or protein mixture was determined as a slope of the linear curve representing the plot. The partition experiments were carried out in duplicate or triplicate.

Several separately prepared test protein mixtures with unidentified composition were subjected to partitioning using the above procedure.

Figure 4:
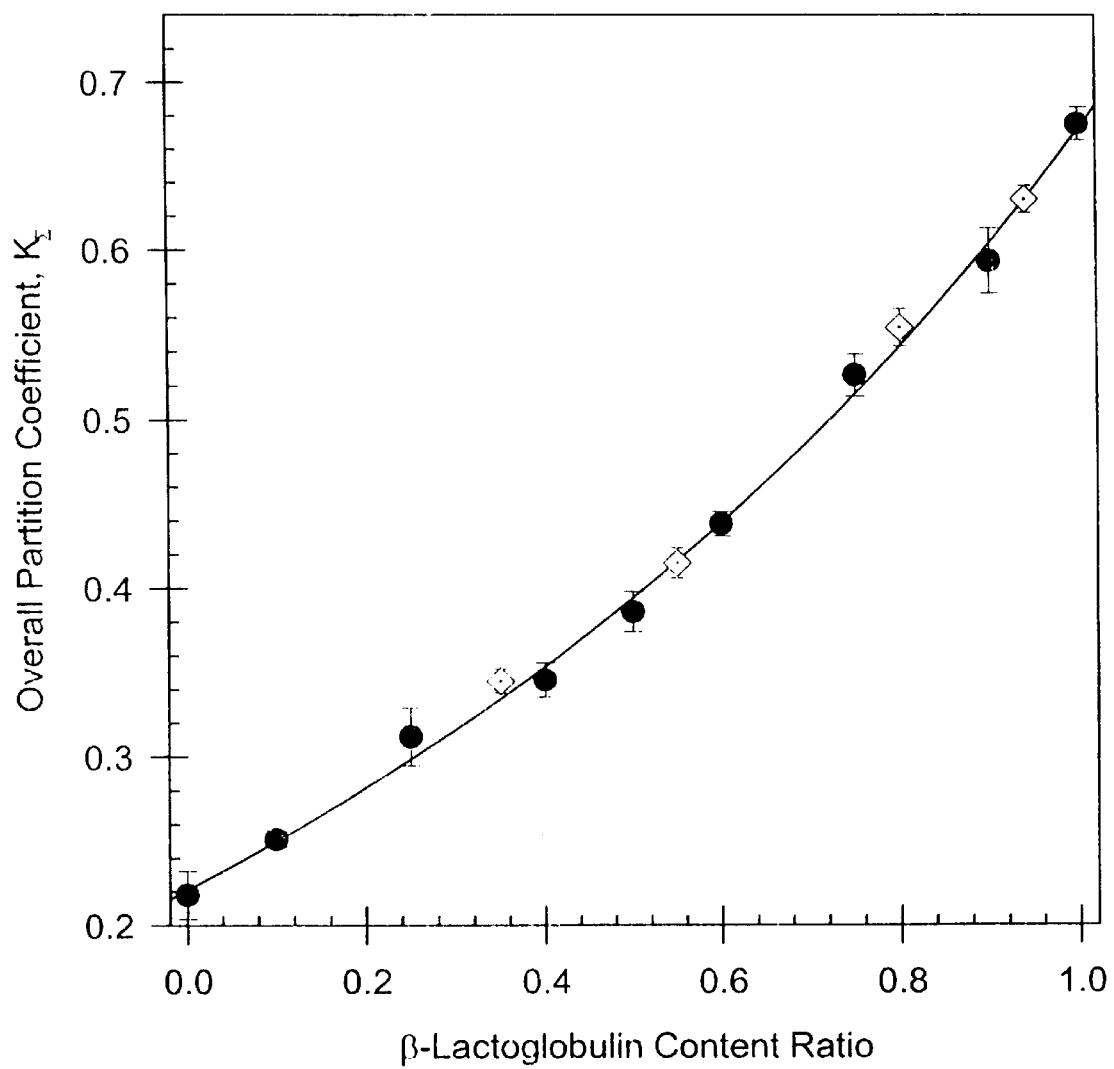
FIG. 4 illustrates the relationship between the overall partition coefficient for the mixture of commercial samples of horse myoglobin and bovine β-lactoglobulin and their ratios in an aqueous two-phase system. The system contained 13.75 wt. % PEG-600 (with molecular weight about 600), 21.00 wt. % sodium/potassium phosphate buffer (pH 6.5). The β-lactoglobulin content ratios were 1:0; 9:1; 3:1; 3:2; 1:1; 2:3; 1:3; 1:9; 0:1. The β-lactoglobulin content ratio was defined as the ratio of the amount of β-lactoglobulin to the total amount of β-lactoglobulin and myoglobin in the mixture (in mg/ml). The protein(s) concentrations in each phase were assayed by measuring the optical absorbance at 280 nm in cuvettes with 10 mm path length. Filled circles represent experimental data obtained with calibration standard mixtures; dotted diamonds represent the experimental data obtained with the separately prepared mixtures of unidentified composition.

The partition coefficients for the examined mixtures of $\beta$-lactoglobulin and myoglobin (represented by filled circles) are plotted in FIG. 4 versus the $\beta$-lactoglobulin content ratio in the mixtures. The $\beta$-lactoglobulin content ratio is calculated as the ratio between the amount of $\beta$-lactoglobulin and the total amount of $\beta$-lactoglobulin and myoglobin in each mixture (in mg/ml). The data given in FIG. 4 clearly indicate that there is a continuous and unique relationship—calibration curve—between the overall partition coefficient for a protein mixture and the ratio of the concentrations of the two components in the mixture. This relationship exists even when both protein components of the mixture partition into the same phase. The partition coefficient values for test mixtures with unidentified composition are represented by dotted diamonds. The compositions of the unidentified test mixtures lie, within experimental error, on the previously constructed calibration curve. Thus, this invention is useful for analysis of proteins as long as there is a measurable difference between the individual partition coefficient values for the two components in the same aqueous system. This invention is useful even when the components partition predominantly into the same phase.

Example 5

Partitioning of mixtures of human hemoglobin and glycated hemoglobin in different aqueous two-phase systems is related to the ratio of the amounts of proteins in the mixture.

The example below demonstrates that the partitioning of a mixture of proteins in any aqueous two- phase system is related to the ratio of the amounts of proteins in the mixture. This is true if the partition coefficients of individual proteins are significantly different and measurable.

Lyophilized preparations of stabilized human blood containing a normal level of glycosylated hemoglobin (Hb $A_1$) and total glycated hemoglobin (GHb) under the trade name "Glycohemoglobin Control-N" and stabilized human blood containing an elevated level of glycosylated hemoglobin (Hb $A_1$) and total glycated hemoglobin (GHb) under the trade name "Glycohemoglobin Control-E" were purchased from Sigma Chemical Company (St. Louis, Mo., USA). The glycosylated hemoglobin in both samples represented a mixture of various isoforms of Hb with different degrees of glycosylation. The ensemble average of these isoforms as a sub-population is considered diagnostically relevant when comparing the two control groups. Stock solutions of these protein preparations were prepared in water according to the procedure recommended by manufacturer with the change that instead of dissolving the preparation in 0.5 ml it was dissolved in 15 to 20 ml of water. These protein solutions were subjected to partitioning in the aqueous polyethylene glycol)-Na/K-phosphate buffer the two-phase systems of pH varied from 6.3 to 6.9. In the aqueous dextran-polyvinylpyrrolidone two-phase system containing 0.15 M NaCl in 0.3 M Na/K-phosphate buffer the pH varied from 4.9 to 7.3. In the aqueous dextran-poly(ethylene glycol) two-phase systems containing 0.15 M Na/K phosphate buffer pH varied from 4.9 to 7.3.

The aqueous two-phase system contained 15.00 wt. % polyvinylpyrrolidone K-15 (with molecular weight of about 15,000), 8.67 wt. % dextran-500 (with molecular weight of about 500,000), and additives of sodium/potassium phosphate buffer and NaCl as indicated in Table 1. The systems were prepared by mixing the appropriate amounts of stock polymer and buffer solutions by weight into a 100×75 mm tube up to a total weight of a system of 2.00 g. The ratio between the volumes of the two phases of each system was (volume of the top phase to volume of the bottom phase) about 1:1. A varied amount (50, 75, and 100 μl) of a given protein preparation solution and the corresponding amount (200, 175, and 150 μl) of water were added to a system. The system was vigorously shaken and centrifuged for 20 min. at about 2000 rpm in a centrifuge with a bucket rotor to speed the phase settling. The tubes were taken out of the centrifuge, and samples from the top and the bottom phases were withdrawn. The aliquots of 50, 75, and 100 μl from the samples of both phases were withdrawn in duplicate and each diluted with water up to 200 μl of total volume of the final sample to be assayed. Preparation of aqueous poly (ethylene glycol)-Na/K-phosphate buffer two-phase systems of pH varied from 6.3 to 8.3. In dextran-poly(ethylene glycol) two-phase systems containing 0.15 M Na/K phosphate buffer, pH varied from 4.9 to 7.3. Systems and partitioning experiments in these systems were performed in the similar manner.

The protein concentrations in each phase were assayed by measuring the optical absorbance at 418 nm in cuvettes with 10 mm path length. The measured absorbance of the aliquots from the top phases were plotted as a function of the absorbance of the aliquots from the bottom phases. The partition coefficient for a given protein preparation was determined as a slope of the linear curve representing the plot. The partition experiments were carried out in duplicate or triplicate.

The partition coefficients for the examined preparations of "Glycohemoglobin Control-N" and "Glycohemoglobin Control-E" are presented in Table 2 together with the content of components as provided by manufacturer. The data given in Table 2 indicates clearly that the changes in the ratio between the amounts of hemoglobin and glycated hemoglobin are reflected in the overall partition coefficient values for the protein preparations examined. It also follows from the data in Table 2 that different aqueous two-phase systems may be employed for the purpose of the present invention, and that the composition of an aqueous two-phase partition system employed is important for differentiating between the protein samples analyzed.

TABLE 2

Overall partition coefficient values for Glycohemoglobin Contorl-N [a] ($K_N$) and Glycohemoglobin Control-E [a] ($K_E$) under different partition conditions.

| Polymer 1 | Polymer 2 | Buffer | pH | Salt additive | $K_N$ | $K_E$ |
|---|---|---|---|---|---|---|
| Dextran 500 | Polyvinyl-pyrrolidone | 0.15 M | 4.9 | 0.15 M NaCl | 0.819 | 0.786 |
| Dextran 500 | Polyvinyl-pyrrolidone | 0.30 M | 5.4 | 0.15 M NaCl | 0.881 | 0.868 |
| Dextran 500 | Polyvinyl-pyrrolidone | 0.30 M | 7.3 | 0.15 M Nacl | 0.573 | 0.634 |
| Dextran 500 | Polyvinyl-pyrrolidone | 0.15 M | 7.3 | 0.15 M Nacl | 1.845 | 1.962 |
| Dextran 500 | PEG-8000 [b] | 0.15 M | 4.9 | — | 0.337 | 0.269 |
| Dextran 500 | PEG-8000 [b] | 0.15 M | 6.5 | — | 0.205 | 0.290 |
| Dextran 500 | PEG-8000 [b] | 0.15 M | 7.3 | — | 0.434 | 0.347 |
| PEG-600 [b] | — | 21.0% wt. | 6.3 | — | 0.645 | 0.825 |
| PEG-600 [b] | — | 21.0% wt. | 6.7 | — | 0.836 | 1.113 |
| PEG-600 [b] | — | 21.0% wt. | 6.9 | — | 2.317 | 2.585 |
| PEG-1000 [b] | — | 16.0% wt. | 7.6 | — | 1.025 | 1.277 |

[a] Glycohemoglobin Control-N contains: 6.5% Hb $A_1$ and 7.6% GHb; Glycohemoglobin Control-E contains: 13.0% Hb $A_1$ and 15.0% GHb.
[b] PEG-8000 - poly(ethlene glycol) with the molecular weight of about 8,000;
PEG-600 - poly(ethlene glycol) with the molecular weight of about 600;
PEG-1000 - poly(ethlene glycol) with the molecular weight of about 1,000.

Example 6

Determination of the ratio of the amounts of proteins in a mixture of human transferrin (Tf) and carbohydrate-deficient transferrin (CDT).

Human iron-saturated transferrin was purchased from Sigma Chemical Company (St. Louis, Mo., USA) and used without further purification. Carbohydrate-deficient transferrin was prepared by treating the transferrin with insoluble neuraminidase from Vibrio Cholerae for 24 hrs at 37° C., according to standard procedure. Desialylation of transferrin was controlled by electrophoresis in polyacrylamide gel according to standard procedure. Stock solutions of transferrin and carbohydrate-deficient transferrin in water were prepared at the protein concentration of 10.0 mg/ml each. Protein stock solutions were mixed with each other to form standard calibration mixtures of the following transferrin/carbohydrate-deficient transferrin ratios: 1:0; 1:5; 2:5; 3:5; 4:5; 0:1. These protein mixtures as well as solutions of individual proteins were subjected to partitioning in the aqueous poly(ethylene glycol)-phosphate buffer two-phase system.

The aqueous two-phase system contained 13.75 wt. % PEG-600 (with molecular weight of about 600) and 21.00 wt. % sodium/potassium phosphate buffer (pH 6.95). Each system was prepared by mixing the appropriate amounts of stock polymer and buffer solutions by weight into a 100 ×75 mm tube up to a total system weight of 2.00 g. The ratio between the volumes of the two phases of each system was 1:1. A varied amount (80, 160, 240, 320, and 400 μl) of a given protein solution or that of a mixture of a given ratio and the corresponding amount (320, 240, 160, 80, and 0 μl) of water were added to a system. The system was vigorously shaken and centrifuged for 30 min. at about 2000 rpm in a centrifuge with a bucket rotor to speed the phase settling. Tubes were taken out of the centrifuge, and aliquots of 200 μl from the top and the bottom phases were withdrawn in duplicate and each diluted with 1.300 ml water for further analysis.

The protein(s) concentrations in each phase were assayed by measuring the optical absorbance at 278 nm in cuvettes with 10 mm path length. The measured absorbance of the aliquots from the top phases were plotted as a function of the absorbance of the aliquots from the bottom phases. The partition coefficient for a given protein or protein mixture was determined as a slope of the linear curve representing the plot. The partition experiments were carried out in duplicate or triplicate.

Several separately prepared test protein mixtures with unidentified composition were subjected to partitioning using the above procedure.

Figure 5:
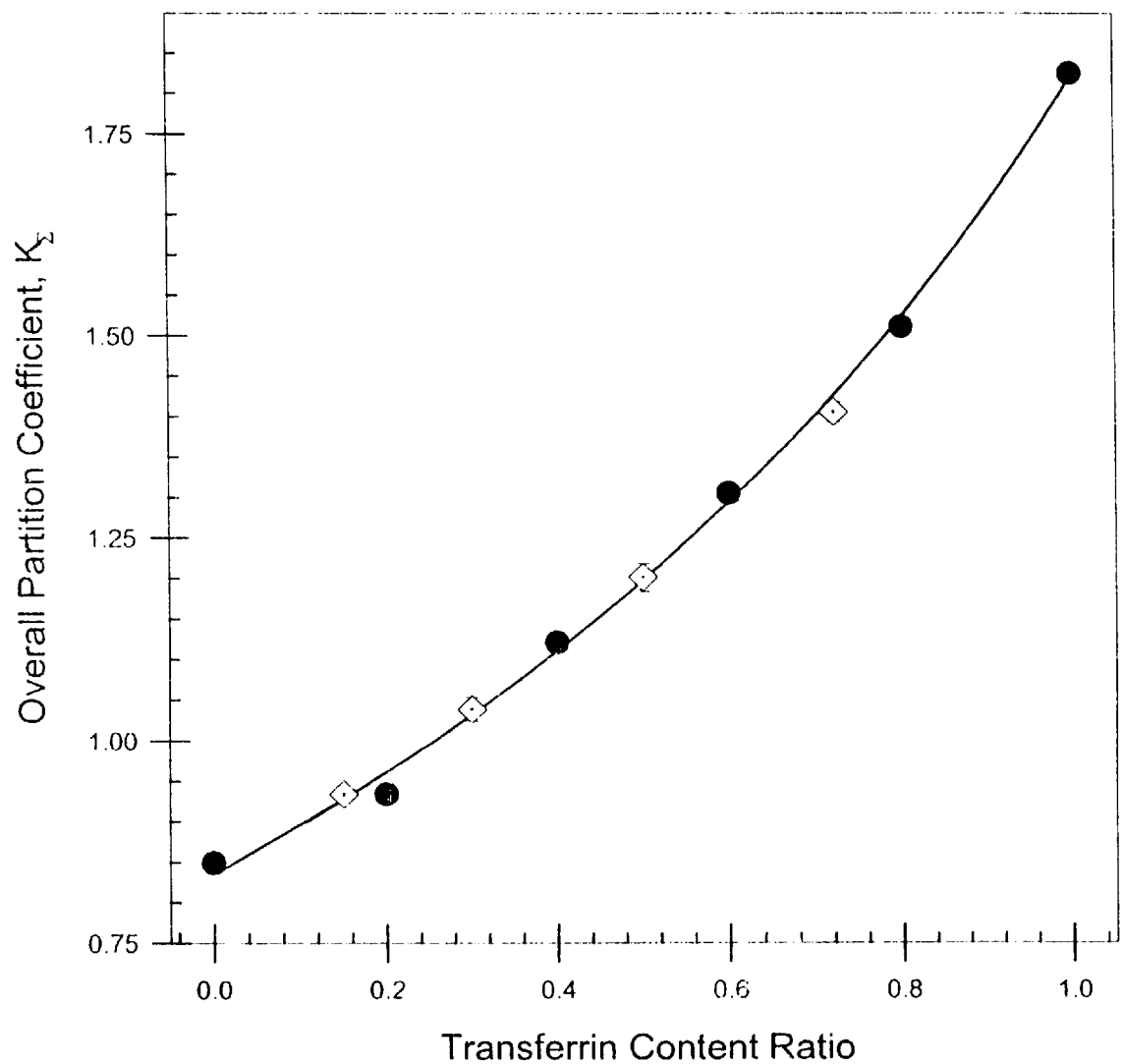
FIG. 5 illustrates the relationship between the overall partition coefficient for the mixture of commercial sample of human transferrin and carbohydrate-deficient transferrin, obtained as described in text, and their ratios in an aqueous two-phase system. The system contained 13.75 wt. % PEG-600 (with molecular weight about 600), 21.00 wt. % sodium/potassium phosphate buffer (pH 6.95). The transferrin content ratios were 1:0; 1:5; 2:5; 3:5; 4:5; 0:1). The transferrin content ratio was defined as the ratio of the amount of transferrin to the total amount of transferrin and carbohydrate-deficient transferrin in the mixture (in mg/ml). The protein(s) concentrations in each phase were assayed by measuring the optical absorbance at 280 nm in cuvettes with 10 mm path length. Filled circles represent experimental data obtained with calibration standard mixtures; dotted diamonds represent the experimental data obtained with the separately prepared mixtures of unidentified composition.

The partition coefficients for the examined standard calibration mixtures of transferrin and carbohydrate-deficient transferrin (represented by filled circles) are plotted in FIG. 5 versus the transferrin content ratio in the mixtures. The transferrin content ratio was calculated as the ratio between the amount of transferrin and the total amount of transferrin and carbohydrate-deficient transferrin in each mixture (in mg/ml). The data given in FIG. 5 indicate clearly that there is a continuous and unique relationship—calibration curve—between the overall partition coefficient for a protein mixture and the ratio of the concentrations of the two components in the mixture. The partition coefficient values for test mixtures with unidentified composition are represented by dotted diamonds. The compositions of the unidentified test mixtures lie, within experimental error, on the previously constructed calibration curve.

Example 7

Determination of the ratio of the amounts of components in a mixture of 2'-deoxyadenosine and adenosine 5'-monophosphate sodium salt.

2'-Deoxyadenosine and adenosine 5'-monophosphate sodium salt were purchased from Sigma Chemical Company (St. Louis, Mo., USA) and used without further purification. A stock solution of 2'-deoxyadenosine in water was prepared at the concentration of 0.48 mg/ml, and a stock solution of adenosine 5'-monophosphate sodium salt in water was prepared at the concentration of 0.67 mg/ml. Stock solutions of individual 2'-deoxyadenosine and adenosine 5'-monophosphate sodium salt were mixed with each other to form standard calibration mixtures of the following volume ratios: 1:0; 9:1; 4:1; 7:3; 3:2; 3:7; 1:4; 0:1. These mixtures as well as solutions of individual compounds were subjected to partitioning in the aqueous poly(ethylene glycol)-sodium sulfate two-phase system.

The aqueous two-phase system contained 14.0 wt. % PEG-8000 (molecular weight of about 8000), 18.80 wt. % sodium sulfate, and 0.01 M sodium phosphate buffer (pH 6.77). Each system was prepared by mixing the appropriate amounts of stock polymer and buffer solutions by weight into a 100 ×75 mm tube up to a total system weight of 2.00 g. The ratio between the volumes of the two phases of each system was 1:1. A varied amount (50, 100, 200, 300, and 400 μl) of a given compound solution or that of a mixture of a given ratio and the corresponding amount (430, 380, 280, 180, and 80 μl) of water were added to a system. The system was vigorously shaken and centrifuged for 20 min. at about 3000 rpm in a refrigerated centrifuge at 20° C. with a bucket rotor to speed the phase settling. Tubes were taken out of the centrifuge, and aliquots of 150 μl from the top and the bottom phases were withdrawn in duplicate and each diluted with 1.0 ml water for further analysis.

The compound(s) concentrations in each phase were assayed by measuring the optical absorbance at 260 nm in cuvettes with 10 mm path length. The measured absorbance of the aliquots from the top phases were plotted as a function of the absorbance of the aliquots from the bottom phases. The partition coefficient for a given compound or mixture of compounds was determined as a slope of the linear curve representing the plot. The partition experiments were carried out in duplicate or triplicate.

Several separately prepared test mixtures of the two compounds with unidentified composition were subjected to partitioning using the above procedure.

Figure 6:
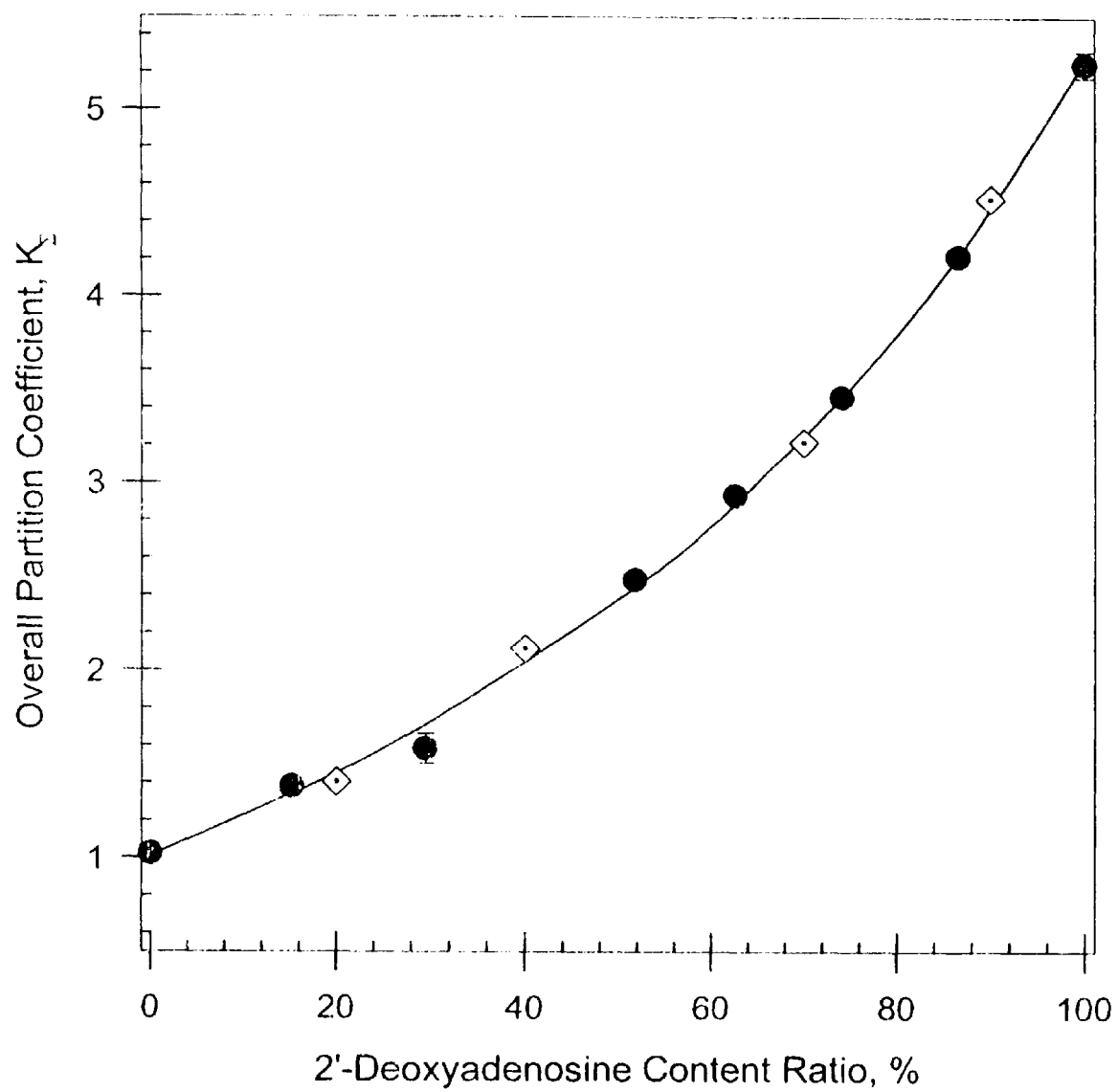
FIG. 6 illustrates the relationship between the overall partition coefficient for the mixture of commercial sample of 2'-deoxyadenosine and adenosine 5'-monophosphate sodium salt and their ratios in an aqueous two-phase system. The system contains 14.0 wt. % PEG-8000 (molecular weight of about 8000), 18.80 wt. % sodium sulfate, and 0.01 M sodium phosphate buffer (pH 6.77). The 2'-deoxyadenosine content ratios were varied from 1:0 to 0:1. The 2'-deoxyadenosine content ratio was defined as the ratio of the amount of 2'-deoxyadenosine to the total amount of 2'-deoxyadenosine and adenosine 5'-monophosphate sodium salt in the mixture (in mg/ml). The concentrations of the compounds in each phase were assayed by measuring the optical absorbance at 260 nm in cuvettes with 10 mm path length. Filled circles represent experimental data obtained with calibration standard mixtures; dotted diamonds represent the experimental data obtained with the separately prepared mixtures of unidentified composition.

The partition coefficients for the examined standard calibration mixtures of 2'-deoxyadenosine and adenosine 5'-monophosphate sodium salt (represented by filled circles) are plotted in FIG. 6 versus the 2'-deoxyadenosine content ratio in the mixtures. The 2'-deoxyadenosine content ratio was calculated as the ratio between the amount of 2'-deoxyadenosine and the total amount of 2'-deoxyadenosine and adenosine 5'-monophosphate sodium salt in each mixture (in mg/ml). The data given in FIG. 6 indicate clearly that there is a continuous and unique relationship—calibration curve—between the overall partition coefficient for a mixture of the compounds and the ratio of the concentrations of the compounds in the mixture. The partition coefficient values for test mixtures with unidentified composition are represented by dotted diamonds. The compositions of the unidentified test mixtures lie, within experimental error, on the previously constructed calibration curve. This example illustrates that the ratio of the components can be analyzed by the technique of the present invention in the mixtures of nucleotides and nucleosides as well as in those of proteins.

Example 8

Determination of the ratio of the amounts of components in a mixture of p-nitrophenyl phosphate and p-nitorphenyl-α-D-mannopyranoside.

Bis-p-nitrophenyl phosphate and p-nitorphenyl-α-D-mannopyranoside were purchased from Sigma Chemical Company (St. Louis, Mo., USA) and used without further purification. A stock solution of bis-p-nitrophenyl phosphate in water was prepared at the concentration of 0.848 mg/ml. A stock solution of p-nitorphenyl-α-D-mannopyranoside in water was prepared at the concentration of 0.426 mg/ml. Stock solutions of individual bis-p-nitrophenyl phosphate and p-nitrophenyl-α-D-mannopyranoside were mixed with each other to form standard calibration mixtures of different volume ratios from 1:0 to 0:1. These mixtures as well as solutions of individual compounds were subjected to partitioning in the aqueous poly(ethylene glycol)-phosphate buffer two-phase system.

The aqueous two-phase system contained 12.50 wt. % PEG-8000 (molecular weight of about 8000) and 11.70 wt. % sodium/potassium phosphate buffer (pH 6.5). Each system was prepared by mixing the appropriate amounts of stock polymer and buffer solutions by weight into a 100 ×75 mm tube up to a total weight of a system of 2.00 g. The ratio between the volumes of the two phases of each system was 1:1. A varied amount (100, 200, 300, 400, and 500 µl) of a given compound solution or that of a mixture of a given ratio and the corresponding amount (810, 710, 610, 510, and 410 µl) of water were added to a system. The system was vigorously shaken and centrifuged for 20 min. at about 3000 rpm in a refrigerated centrifuge at 20° C. with a bucket rotor to speed the phase settling. The tubes were taken out of the centrifuge, and aliquots of 150 µl from the top and the bottom phases were withdrawn in duplicate and each diluted with 1.0 ml water for further analysis.

The compound(s) concentrations in each phase were assayed by measuring the optical absorbance at 300 nm in cuvettes with 10 mm path length. The measured absorbance of the aliquots from the top phases were plotted as a function of the absorbance of the aliquots from the bottom phases. The partition coefficient for a given compound or mixture of compounds was determined as a slope of the linear curve representing the plot. The partition experiments were carried out in duplicate or triplicate.

Several separately prepared test mixtures of the two compounds with unidentified composition were subjected to partitioning using the above procedure.

Figure 7:
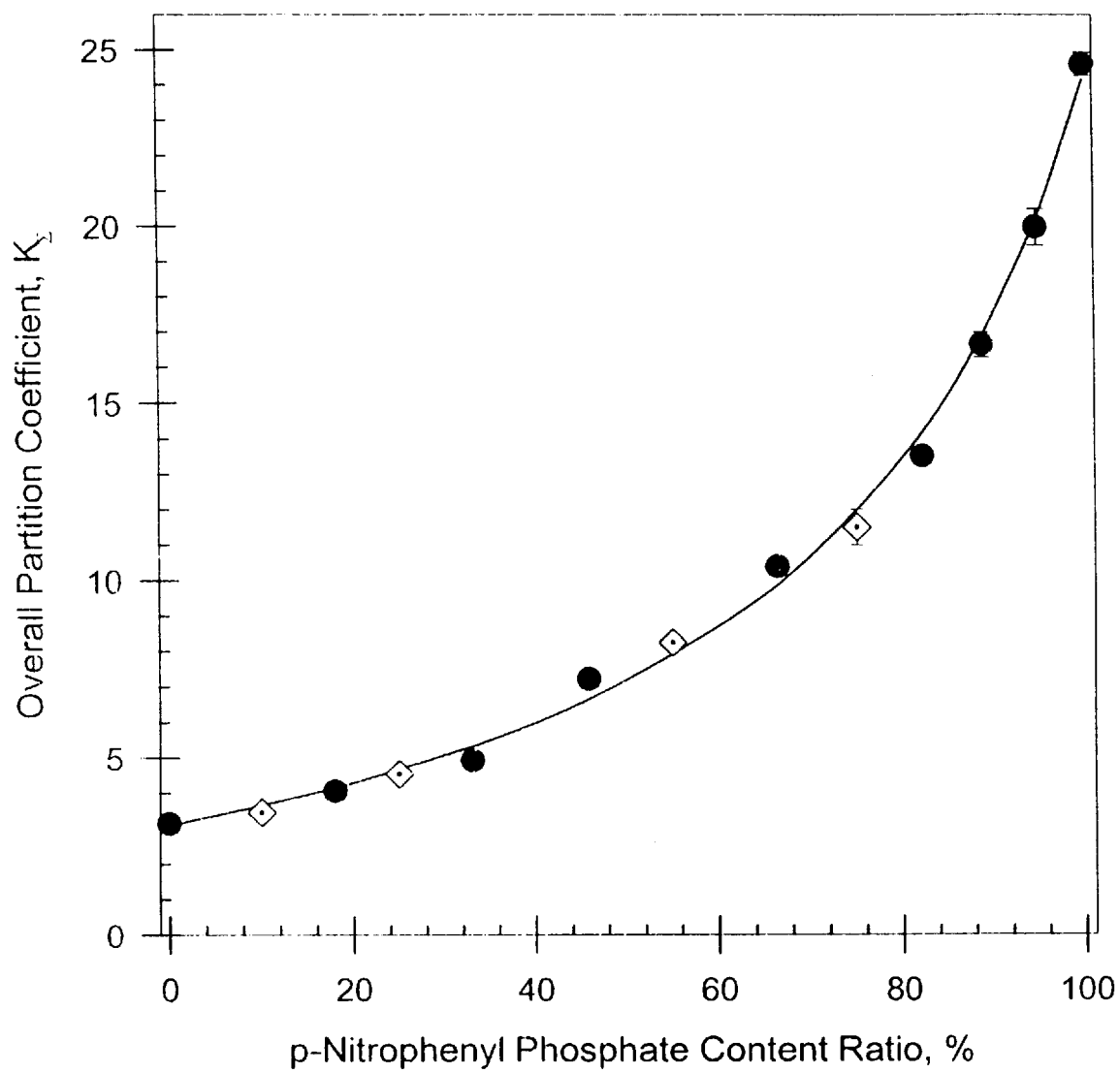
FIG. 7 illustrates the relationship between the overall partition coefficient for the mixture of commercial sample of bis-p-nitrophenyl phosphate and p-nitorphenyl-α-D-mannopyranoside and their ratios in an aqueous two-phase system. The system contained 12.50 wt. % PEG-8000 (with molecular weight of about 8000) and 11.70 wt. % sodium/potassium phosphate buffer (pH 6.5). The bis-p-nitrophenyl phosphate content ratios varied from 1:0 to 0:1. The bis-p-nitrophenyl phosphate content ratio was defined as the ratio of the amount of bis-p-nitrophenyl phosphate to the total amount of bis-p-nitrophenyl phosphate and p-nitorphenyl-α-D-mannopyranoside in the mixture (in mg/ml). The concentrations of the compounds in each phase were assayed by measuring the optical absorbance at 300 nm in cuvettes with 10 mm path length. Filled circles represent experimental data obtained with calibration standard mixtures; dotted diamonds represent the experimental data obtained with the separately prepared mixtures of unidentified composition.

The partition coefficients for the examined standard calibration mixtures of bis-p-nitrophenyl phosphate and p-nitrophenyl-α-D-mannopyranoside (represented by filled circles) are plotted in FIG. 7 versus the bis-p-nitrophenyl phosphate content ratio in the mixtures. The bis-p-nitrophenyl phosphate content ratio was calculated as the ratio between the amount of bis-p-nitrophenyl phosphate and the total amount of bis-p-nitrophenyl phosphate and p-nitrophenyl-α-D-mannopyranoside in each mixture (in mg/ml). The data given in FIG. 7 indicate clearly that there is a continuous and unique relationship—calibration curve—between the overall partition coefficient for a mixture of the compounds and the ratio of the concentrations of the compounds in the mixture. The partition coefficient values for test mixtures with unidentified composition are represented by dotted diamonds. The compositions of the unidentified test mixtures lie, within experimental error, on the previously constructed calibration curve. This example indicates that the ratio of the components can be analyzed by the present invention in mixtures of compounds of any chemical nature including those of low molecular weight.

Example 9

Determination of the ratio of the amounts of components in a mixture of p-nitrophenyl phosphate and p-nitorphenyl-α-D-mannopyranoside.

Bis-p-nitrophenyl phosphate and p-nitorphenyl-α-D-mannopyranoside were purchased from Sigma Chemical Company (St. Louis, Mo., USA) and used without further purification. Stock solution of bis-p-nitrophenyl phosphate in water was prepared at the concentration of 0.848 mg/ml, and stock solution of p-nitorphenyl-α-D-mannopyranoside in water was prepared at the concentration of 0.426 mg/ml. Stock solutions of individual bis-p-nitrophenyl phosphate and p-nitorphenyl-α-D-mannopyranoside were mixed with each other to form standard calibration mixtures of different volume ratios varied from 1:0 to 0:1. These mixtures as well as solutions of individual compounds were subjected to partitioning in the aqueous poly(ethylene glycol)-phosphate buffer two-phase system.

The aqueous two-phase system contained 13.33 wt. % PEG-600 (molecular weight of about 600) and 20.29 wt. % sodium/potassium phosphate buffer (pH 6.5). Each system was prepared by mixing the appropriate amounts of stock polymer and buffer solutions by weight into a 100×75 mm tube up to a total weight of a system of 2.00 g. The ratio between the volumes of the two phases of each system was 1:1. A varied amount (100, 200, 300, 400, and 500 µl) of a given compound solution or that of a mixture of a given ratio and the corresponding amount (440, 340, 240, 140, and 40 µl) of water were added to a system. The system was vigorously shaken and centrifuged for 40 min. at about 3000 rpm in a refrigerated centrifuge at 20° C. with a bucket rotor to speed the phase settling. Tubes were taken out of the centrifuge, and aliquots of 80 µl from the top and 200 µl from the bottom phases were withdrawn in duplicate and each diluted with 1.0 ml water for further analysis.

The compound(s) concentrations in each phase were assayed by measuring the optical absorbance at 300 nm in cuvettes with 10 mm path length. The measured absorbance of the aliquots from the top phases were plotted as a function of the absorbance of the aliquots from the bottom phases. The partition coefficient for a given compound or mixture of compounds was determined as a slope of the linear curve representing the plot. The partition experiments were carried out in duplicate or triplicate.

Several separately prepared test mixtures of the two compounds with unidentified composition were subjected to partitioning using the above procedure.

Figure 8:
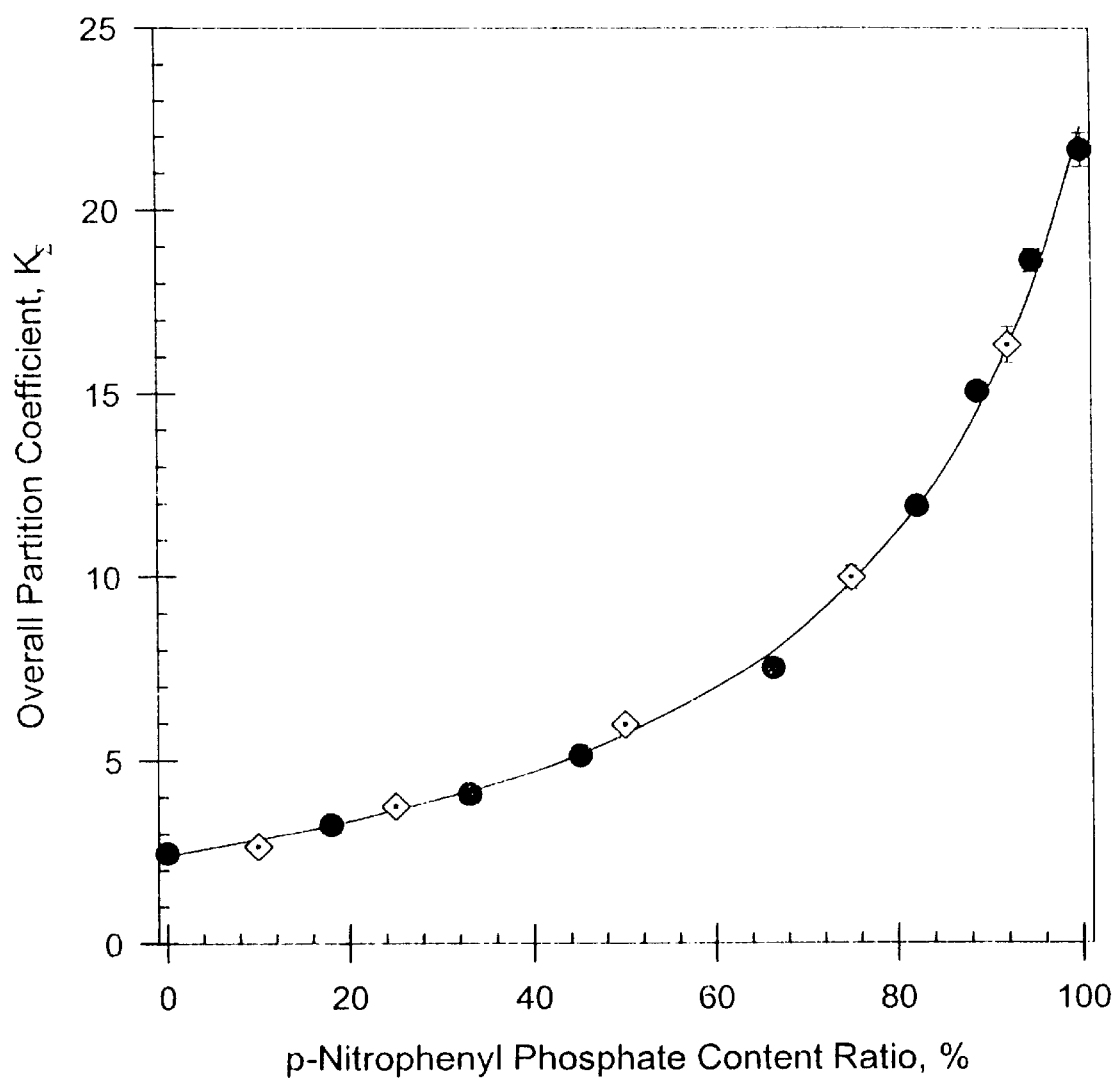
FIG. 8 illustrates the relationship between the overall partition coefficient for the mixture of a commercial sample of bis-p-nitrophenyl phosphate and p-nitorphenyl-α-D-mannopyranoside and their ratios in an aqueous two-phase system. The system contained 13.33 wt. % PEG-600 (molecular weight of about 600) and 20.29 wt. % sodium/potassium phosphate buffer (pH 6.5) The bis-p-nitrophenyl phosphate content ratios varied from 1:0 to 0:1. The bis-p-nitrophenyl phosphate content ratio was defined as the ratio of the amount of bis-p-nitrophenyl phosphate to the total amount of bis-p-nitrophenyl phosphate and p-nitorphenyl-α-D-mannopyranoside in the mixture (in mg/ml). The concentrations of the compounds in each phase were assayed by measuring the optical absorbance at 300 nm in cuvettes with 10 mm path length. Filled circles represent experimental data obtained with calibration standard mixtures; dotted diamonds represent the experimental data obtained with the separately prepared mixtures of unidentified composition.

The partition coefficients for the examined standard calibration mixtures of bis-p-nitrophenyl phosphate and p-nitrophenyl-α-D-mannopyranoside (represented by filled circles) are plotted in FIG. 8 versus the bis-p-nitrophenyl phosphate content ratio in the mixtures. The bis-p-nitrophenyl phosphate content ratio was calculated as the ratio between the amount of bis-p-nitrophenyl phosphate and the total amount of bis-p-nitrophenyl phosphate and p-nitrophenyl-α-D-mannopyranoside in each mixture (in mg/ml). The data given in FIG. 8 indicate clearly that there is a continuous and unique relationship—calibration curve—between the overall partition coefficient for a mixture of the compounds and the ratio of the concentrations of the compounds in the mixture. The partition coefficient values for test mixtures with unidentified composition are represented by dotted diamonds. The compositions of the unidentified test mixtures lie, within experimental error, on the previously constructed calibration curve. This example together with example 8 indicate that the ratio of the components can be analyzed by the present invention in aqueous two phase systems formed by inorganic salts and polymers of different molecular weights.

The generality (but not the novelty) of the present invention is further illustrated by considering the following theoretical analysis of the process of partitioning of a solute (e.g., protein) in a two-phase aqueous system. The following equations describe the mass conservation law for each solute in the system, together with the definition of the partition coefficient for each solute and the subsequent definition of the overall partition coefficient.

In a system comprised of two aqueous phases, the volume fraction of the top phase is denoted by $V_t$, and the volume fraction of the bottom phase by $V_b$. The concentration of the first protein in the top phase is denoted by $C_{1t}$, and in the bottom phase by $C_{1b}$. In this system, the mass conservation equation for the total amounts of the first protein $C_1$ is expressed as:

$$C_{1t}V_t + C_{1b}V_b = C_1$$

Similarly, for the second protein mass conservation we have:

$$C_{2t}V_t + C_{2b}V_b = C_2$$

For each of the two proteins we define a partition coefficient that is unique to the system and the protein in question:

$$K_1 = \frac{C_{1t}}{C_{1b}}$$

$$K_2 = \frac{C_{2t}}{C_{2b}}$$

And for the overall partition coefficient for both proteins we define:

$$K_\Sigma = \frac{C_{1t} + C_{2t}}{C_{1b} + C_{2b}}$$

Finally, the ratio of protein 1 to the total protein concentration is defined as:

$$R = \frac{C_1}{C_1 + C_2}$$

Using algebra, we eliminate the concentration variables from the above equations and arrive at:

$$K_\Sigma = \frac{K_2 V_b + K_1 K_2 V_t + V_b(K_1 - K_2)R}{V_b + V_t K_1 + V_t(K_2 - K_1)R} = \frac{A + BR}{C + DR}$$

In this equation, A,B,C and D are constants related only to the individual K-values and volume fractions. The last equation between $K_\Sigma$ and R demonstrates a unique, single-valued functional relationship between the two variables $K_\Sigma$ and R. Given the partition coefficients of the individual proteins that were independently measured, $K_1$ and $K_2$, and the volume fractions of the two phases, $V_t$ and $V_b$, a unique calibration curve describing the relationship between R and $K_\Sigma$ could be theoretically constructed for any two compounds or their sub-populations in the system as described below.

Example 10

Comparison between experimental data described in Example 3 and the theoretical relationship between $K_\Sigma$ and R as shown in the previous analysis.

For the system in Example 3, $V_t = V_b$ and the values of the individual partition coefficients were:

$$K_{lysozyme} = 7.287 \pm 0.309$$

$$K_{hemoglobin} = 0.959 \pm 0.015$$

The ratio of the two proteins is defined as $$R = \frac{C_{lysozyme}}{C_{lysozyme} + C_{hemoglobin}}$$

The overall partition coefficient for this particular case becomes:

$$K_\Sigma = \frac{7.947 + 6.328R}{8.287 - 6.328R}$$

Figure 9:
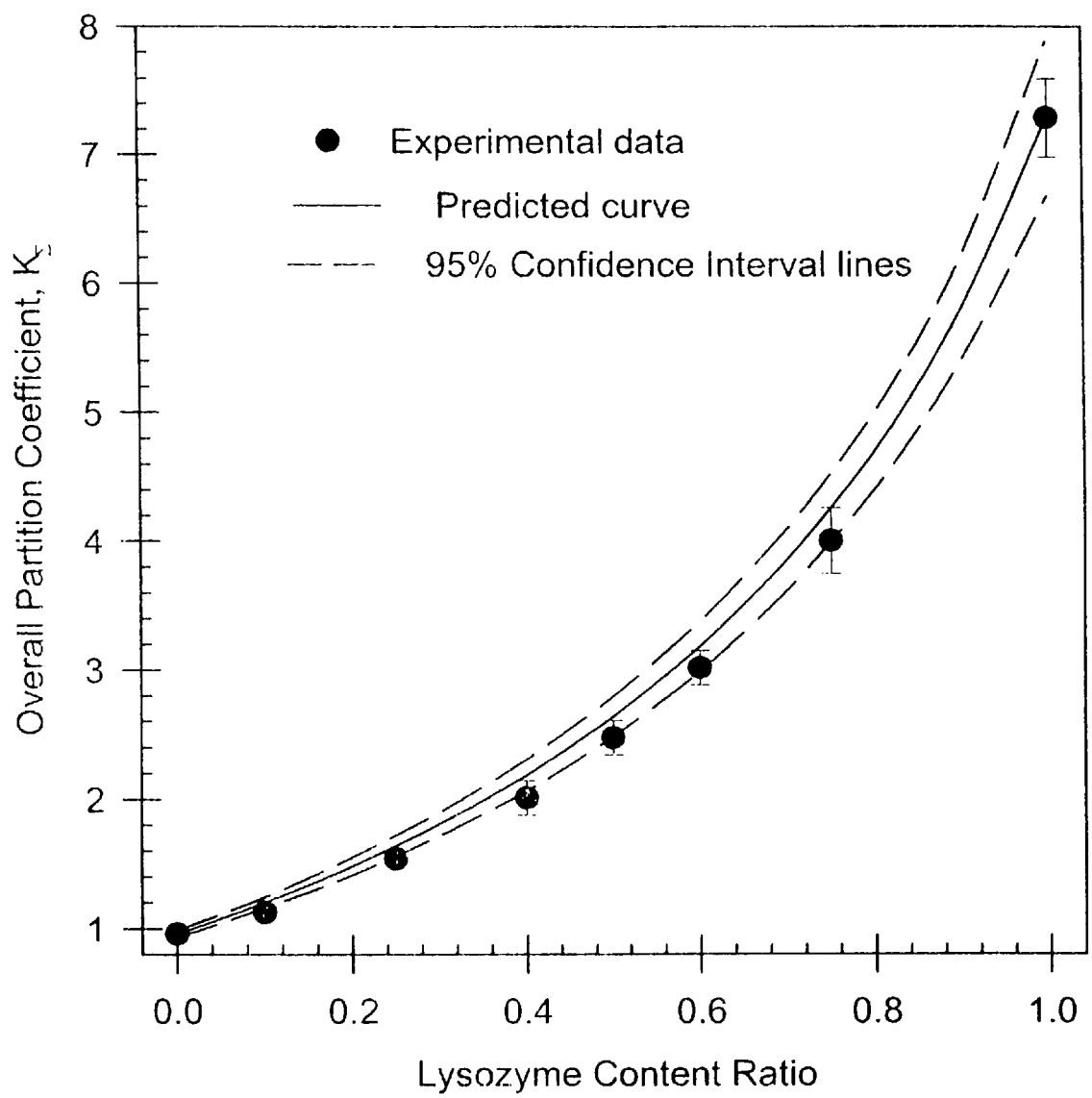
FIG. 9 illustrates the fit between the experimental partition coefficient values for the mixtures of lysozyme and hemoglobin and their ratios obtained as described in Example 3, and the theoretical curve calculated from the data found in separate experiments as described in Example 10. The solid line represents the theoretical curve, the dashed lines represent the upper and lower 95% confidence intervals around the theoretical curve, and the solid circles with error bars represent the experimental data points.

FIG. 9 illustrates the comparison between the experimental data (with the associated error bars) from Example 3 and the theoretical relationship. The theoretical and experimental curves both show a unique (non multi-valued) relationship between $K_\Sigma$ and R. The numerical data from both sources matches within the experimental error bars. The importance of this combined theoretical-experimental example is in establishing the generality of the method that, together with the previous experimental examples, illustrate the application of the invention as a determinant of the ratios of different protein systems from the measurement of their overall partition coefficient values.

Example 11

Determination of the ratio of the amount of carbohydrate-deficient transferrin (CDT) to the amount of total transferrin (Tf) in human blood plasma for monitoring alcohol abuse.

Samples of blood were obtained from Caucasian male volunteer patients entering a drug and alcohol detoxification unit in Cleveland, Ohio. Sample identification was maintained via a control number assigned by the unit. The presumed-positive (hereafter "positive") status was ascertained via an oral interview according to the literature definition as exceeding 60 g/day alcohol consumption for a prolonged period of time. Negative control blood samples were obtained from Caucasian male and female volunteers, either non-drinkers or social drinkers. In each case blood was collected using standard tubes for plasma (with sodium citrate additive). Plasma was subsequently isolated using standard procedures. All samples were stored frozen at $-20°$ C. until use. Each sample (200 $\mu l$) was mixed with 400 $\mu l$ phosphate buffer saline (0.15 M NaCl in 0.01 M sodium phosphate buffer, pH 7.3) and subjected to partitioning in the aqueous poly(ethylene glycol)-phosphate buffer two-phase system.

The aqueous two-phase system contained 13.75 wt. % PEG-600 (with molecular weight of about 600) and 21.00 wt. % sodium/potassium phosphate buffer (pH 6.95). Each system was prepared by mixing the appropriate amounts of stock polymer and buffer solutions by weight into a 100×75 mm tube up to a total weight of a system of 2.00 g. The ratio between the volumes of the two phases of each system was as 1:1. Each 150 $\mu l$ diluted plasma sample was added to a system. The system was vigorously shaken and centrifuged for 30 min. at about 2000 rpm in a refrigerated centrifuge with a bucket rotor to speed the phase settling. Tubes were taken out of the centrifuge, and aliquots of 350 $\mu l$ from the top and the bottom phases were withdrawn in duplicate. Aliquots from top phase were diluted with phosphate buffer saline in the volume ratio of 1:100, and aliquots from bottom phase were diluted with water in the volume ratio of 1:200 for further analysis.

The total Tf concentrations in each phase were measured by the heterogeneous solid-phase competitive enzyme immunoassay test "CDT Micro-Plate EIA" manufactured by STC Technologies, Inc. (Bethlehem, Pa.). Calibration curves for each phase were determined using separately prepared standards (solutions of known amounts of human transferrin in top and bottom phases). Anti-human Tf conjugate was diluted 1:14,000. The dynamic range of the assay was 50–5000 ng/ml, with the corresponding absorbance range of 1.1–0.4 OU at 450 nm detection and 492 nm reference.

Normalization of K-values obtained was performed by dividing the K-values of each positive sample by the K-value of a known negative control sample that was processed together with the positive sample. Negative control samples were measured in each microtiter plate to reduce plate-to-plate variability. Three separate partition experiments were performed for each sample. Each aliquot from the top and bottom phase was assayed two or three times. The absorbance readings from these duplicates were averaged before determining the protein concentration from the calibration curve and calculating the K-value. The total variability was typically about 5% for the relative standard deviation of the Tf concentration readings in each phase.

Figure 10:
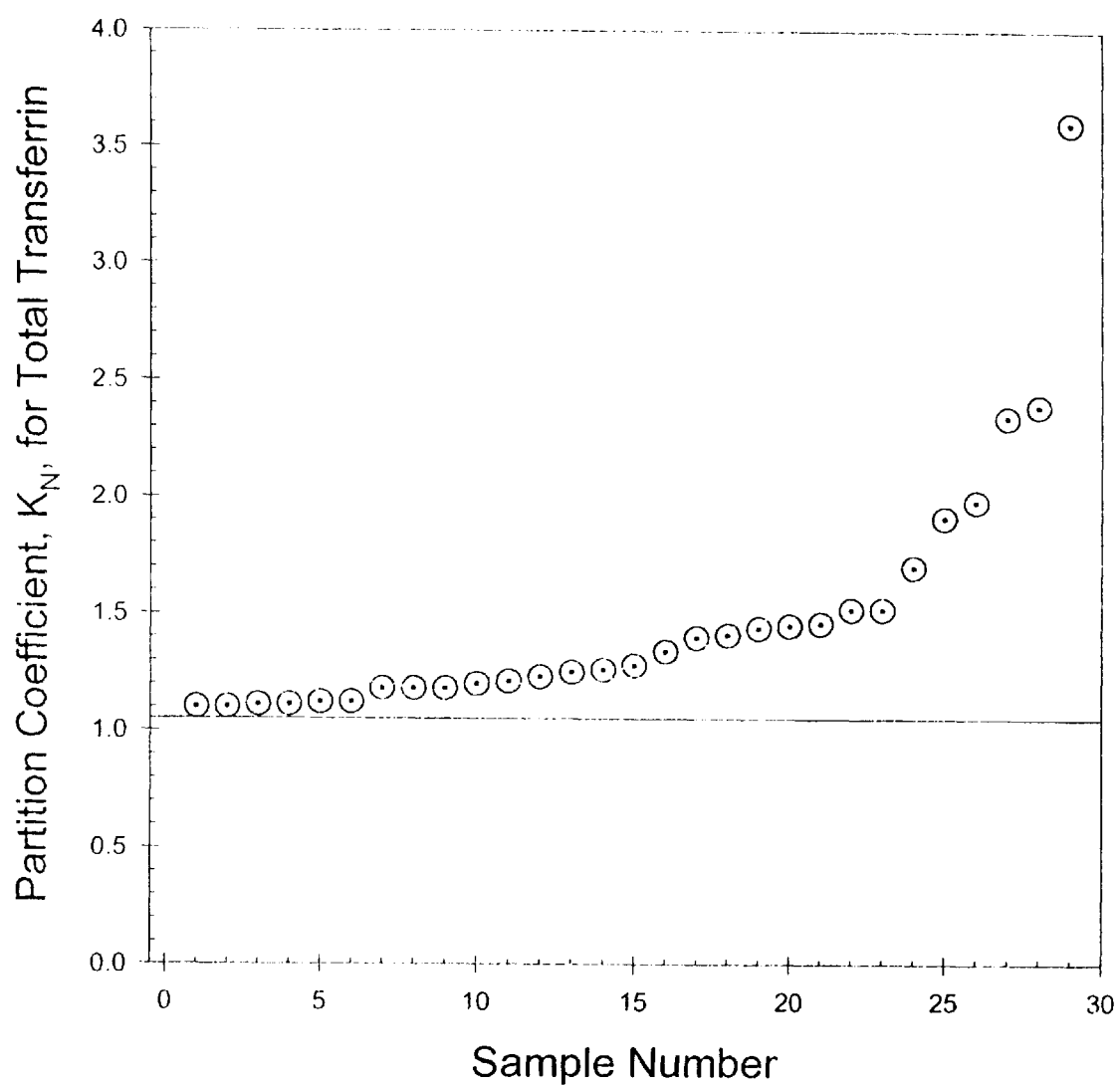
FIG. 10 illustrates the range of partition coefficient for different sub-populations of carbohydrate deficient transferrin (CDT) obtained directly in blood plasma from presumed positive patients with heavy consumption of alcohol. The aqueous two-phase system contained 13.75 wt. % PEG-600 (with molecular weight of about 600) and 21.00 wt. % sodium/potassium phosphate buffer (pH 6.95). The plasma samples where isolated using standard procedures and each sample (200 µl) was mixed with 400 µl phosphate buffer saline (0.15 M NaCl in 0.01 M sodium phosphate buffer, pH 7.3). Following partitioning, aliquots from top phase were diluted with phosphate buffer saline in the volume ratio of 1:100, and aliquots from bottom phase were diluted with water in the volume ratio of 1:200 for further analysis. The total Tf concentrations in each phase were measured by the heterogeneous solid-phase competitive enzyme immunoassay test "CDT Micro-Plate EIA" manufactured by STC Technologies, Inc. (Bethlehem, Pa.). Calibration curves for each phase were determined using separately prepared standards (solutions of known amounts of human transferrin in top and bottom phases). Anti-human Tf conjugate was diluted 1:14,000. The dynamic range of the assay was 50–5000 ng/ml, with the corresponding absorbance range of 1.1–0.4 OU at 450 nm detection and 492 nm reference. Also illustrated is the use of a cut-off value (shown as 1.05) to discriminate between positive samples (here K>1.05) and negative ones in a clinical diagnostic application.

FIG. 10 depicts the K-values of the individual positive samples with presumed elevated levels of CDT subpopulation. It is clear that there is a substantial range in the data, reflecting the internal composition of each sample with different amounts of the various of isoforms, presumably due to different degrees of alcohol consumption. The utility of using the ensemble-average K-value of the entire subpopulation of each sample lies in its magnitude relative to that obtained from negative samples (by definition, unity). Thus, considering the inherent precision level in the experimental procedure, one can designate a certain cut-off value for the K-value (1.05 shown in FIG. 10) where it is presumed that a sample with its K>cut-off value means a positive sample under limitations typical for these applications (e.g., gender and race specific).

This example indicates the utility of using the present invention to examine the relative composition of a sub-population of structurally-similar biomolecules in a complex matrix. It is also shown how the present invention can be used as a clinical diagnostic tool by comparing the K-value of a total-population to a known negative standard.

The results illustrated by the above examples demonstrate that the aqueous two-phase partition technique can be used as a highly sensitive, reliable, simple, and inexpensive method for characterization and analysis of the ratios of proteins and other biological materials and chemical compounds in a mixture. The data and theory indicate that the overall partition coefficient of a mixture of components such as different proteins is uniquely related to the ratio of the components in the mixture. The method could also be used for the analysis of ratio of sub-populations of such compounds, when the ratio is interpreted as the ratio of the ensemble average of each sub-population. Accordingly, the partition technique of the present invention may be used as an analytical method for characterization, quality control, and analysis of the ratio of two or more biopolymers in a multi-component mixture, extract, system, etc.

The invention has been described with reference to the preferred embodiment. Obviously, modifications and alterations will occur to others upon a reading and understanding of the preceding detailed description. It is intended that the invention be construed as including all such alterations and modifications insofar as they come within the scope of the appended claims or the equivalents thereof.

We claim:

1. A method for the quantitative analysis of a multi-component mixture wherein the method of quantitative analysis comprises the steps of:
   i) forming a partitioning system capable of separation into two or more immiscible phases,
   ii) mixing a sample of the mixture to be quantitatively analyzed with the partitioning system;
   iii) maintaining the partitioning system of step (ii) until phase separation occurs;
   iv) measuring the total amount or total concentration of components in the mixture, or of a single class of components within said mixture, in each of the separated phases wherein each of the components being analyzed in the mixture exists in each of the separated phases;
   v) determining the overall partition coefficient (K) of the mixture, or of the single class of components within the mixture, wherein the overall partition coefficient (K) of the mixture is defined as the ratio between the amount or concentrations of the mixture, or the single class of components within the mixture, in each of the separated phases; and,
   vi) comparing the determined overall partition coefficient (K) of the mixture, or the single components within the mixture, with a range of overall partition coefficients obtained from known reference mixtures of the same components thereby assessing the ratio of the particular components of the mixture under characterization without the need to pre-separate the components.

2. The method of claim 1 wherein the pH in the mixture under analysis is within the range of pH from 1.0 to 11.0.

3. The method of claim 1 wherein the phases are of aqueous nature.

4. The method of claim 1 wherein the total weight of the initial mixture being partitioned does not exceed 20 % wt. of the total two-phase system weight.

5. The method of claim 1 wherein the partition coefficient of the overall mixture is measured with a total assay technique wherein said assay techniques comprise dye-based assays, organic nitrogen technique, direct spectrophotometry, and derivatization-based techniques.

6. The method of claim 1 wherein the partition coefficient of a single class of components within the mixture is measured with immunoassay, enzyme activity assay, or biospecific assay.

7. The method of claim 1 wherein the overall partition coefficient of a single class of components within the mixture is used as a measure of the ratio of the amount or concentration of the single class of components of the mixture.

8. The method of claim 1 wherein the temperature of the partitioning system is in the range of 4° C. to 60° C.

9. The method of claim 1 wherein the composition of the partitioning system provides a quantitative relationship between the overall partition coefficient of the mixture and the ratio between the amount or concentration of the components of interest.

10. The method of claim 1 wherein the partition coefficient is measured for the sample of a said mixture in two or more aqueous two-phase systems of different compositions selected from the group consisting of a polymer/polymer system and a polymer/salt system.

11. The method of claim 1 wherein the partitioning system used for partitioning of the mixture is calibrated with partition coefficients (K) for a specifically selected set of low and high molecular weight compounds in addition to the reference samples.

12. The method of claim 1 wherein the overall partition coefficient of the multi-component mixture is used as an indicator of changes in the ratios of the amount or concentration of the components or as an indicator of differences in the multi-component mixture being analyzed relative to those in the mixture used as a reference standard.

13. The method of claim 1 wherein the multi-component mixture is a protein mixture.

14. The method of claim 13 wherein the protein mixture is selected from the group consisting of lysosome/concanavalin A, serum albumin/human γ-globulin, lysosome/hemoglobin, myoglobin/β-lactoglobulin, hemoglobin/glycated hemoglobin, transferrin/carbohydrate-deficient transferrin and Z'-deoxyadenosine/adenosine 5'-monophosphate sodium salt protein mixtures.

15. The method of claim 1 wherein the multi-component mixture is a mixture of biopolymers or sub-populations of said biopolymers.

* * * * *